United States Patent
Mark et al.

(10) Patent No.: US 9,820,480 B2
(45) Date of Patent: Nov. 21, 2017

(54) SYSTEM FOR COLLECTING AND PRESERVING TISSUE CORES

(71) Applicant: Nico Corporation, Indianapolis, IN (US)

(72) Inventors: Joseph L. Mark, Indianapolis, IN (US); Brian C. Dougherty, Terre Haute, IN (US); Mick Trompen, Westfield, IN (US)

(73) Assignee: Nico Corporation, Indianapolis, IN (US)

(*) Notice: Subject to any disclaimer, the term of this patent is extended or adjusted under 35 U.S.C. 154(b) by 344 days.

(21) Appl. No.: 13/835,813

(22) Filed: Mar. 15, 2013

(65) Prior Publication Data
US 2014/0017771 A1   Jan. 16, 2014

Related U.S. Application Data

(63) Continuation-in-part of application No. 13/744,084, filed on Jan. 17, 2013, now Pat. No. 9,504,247, which
(Continued)

(51) Int. Cl.
*A01N 1/02* (2006.01)
*A61B 10/02* (2006.01)
(Continued)

(52) U.S. Cl.
CPC ......... *A01N 1/0284* (2013.01); *A01N 1/0263* (2013.01); *A61B 10/0275* (2013.01);
(Continued)

(58) Field of Classification Search
CPC .................. A01N 1/0284; A61B 10/0275
See application file for complete search history.

(56) References Cited

U.S. PATENT DOCUMENTS 2,044,823 A    6/1936   Whiteside
D161,178 S   12/1950   Waldron
(Continued)

FOREIGN PATENT DOCUMENTS

AU    2011253790 A1    1/2012
EP       125070 A2    11/1984
(Continued)

OTHER PUBLICATIONS

Naylor, et al., Personalized Medicine, 2010, "Unraveling human complexity and disease with systems biology and personalized medicine."
(Continued)

*Primary Examiner* — Sean Dougherty
(74) *Attorney, Agent, or Firm* — Kristin L. Murphy; Brooks Kushman P.C.

(57) ABSTRACT

A thermal system for preserving tissue is disclosed. The cooling system comprises a base member, a temperature control sleeve constructed of a thermally conductive material, and a selectively removable lid member. The base member defines a reservoir and receives the temperature control sleeve. The temperature control sleeve at least partially defines a tissue collector chamber that is configured to receive a tissue collector. The temperature control sleeve is in communication with the reservoir. The reservoir is configured to receive a cooling medium. A slit formed within the tissue collection chamber that is sized to receive a tubing connected to the tissue collector therethrough. The lid member is configured to be selectively attached to the base member, and permit access to a tube mount for the tissue collector when the lid is attached to the base member.

12 Claims, 14 Drawing Sheets

Related U.S. Application Data is a continuation-in-part of application No. 13/352,069, filed on Jan. 17, 2012, now Pat. No. 9,279,751, which is a continuation-in-part of application No. 12/475,258, filed on May 29, 2009, now Pat. No. 9,216,031, which is a continuation-in-part of application No. 12/435,724, filed on May 5, 2009, now Pat. No. 8,460,327, which is a continuation-in-part of application No. 12/404,407, filed on Mar. 16, 2009, now Pat. No. 8,496,599, which is a continuation-in-part of application No. 12/391,579, filed on Feb. 24, 2009, now Pat. No. 8,702,738, which is a continuation-in-part of application No. 12/389,447, filed on Feb. 20, 2009, now Pat. No. 9,655,639, which is a continuation-in-part of application No. 12/336,054, filed on Dec. 16, 2008, now Pat. No. 8,430,825, which is a continuation-in-part of application No. 12/336,086, filed on Dec. 16, 2008, now Pat. No. 8,657,841.

(51) Int. Cl.
| | | |
|---|---|---|
| A61B 17/32 | (2006.01) | |
| A61B 17/3207 | (2006.01) | |
| A61B 17/00 | (2006.01) | |
| A61B 18/00 | (2006.01) | |
| A61B 90/40 | (2016.01) | |

(52) U.S. Cl.
CPC .... *A61B 10/0283* (2013.01); *A61B 17/32002* (2013.01); *A61B 17/320783* (2013.01); *A61B 90/40* (2016.02); *A61B 2010/0208* (2013.01); *A61B 2010/0225* (2013.01); *A61B 2017/00017* (2013.01); *A61B 2017/00977* (2013.01); *A61B 2018/00005* (2013.01); *A61B 2217/005* (2013.01); *A61B 2217/007* (2013.01)

(56) References Cited

U.S. PATENT DOCUMENTS

| | | | | |
|---|---|---|---|---|
| 4,071,029 | A | 1/1978 | Richmond et al. | |
| 4,210,146 | A | 7/1980 | Banko | |
| 4,314,450 | A | 2/1982 | Pelioux-Gervais | |
| 4,493,698 | A | 1/1985 | Wang et al. | |
| 4,650,460 | A | 3/1987 | Roizenblatt | |
| 4,770,654 | A | 9/1988 | Rogers et al. | |
| 4,940,061 | A | 7/1990 | Terwilliger et al. | |
| 5,085,658 | A | 2/1992 | Meyer | |
| 5,098,426 | A | 3/1992 | Sklar et al. | |
| 5,195,541 | A | 3/1993 | Obenchain | |
| 5,337,911 | A * | 8/1994 | Holub | A45C 11/20 16/383 |
| 5,403,276 | A | 4/1995 | Schechter et al. | |
| 5,411,513 | A | 5/1995 | Ireland et al. | |
| 5,415,169 | A | 5/1995 | Siczek et al. | |
| 5,456,689 | A | 10/1995 | Kresch et al. | |
| 5,643,304 | A | 7/1997 | Schechter et al. | |
| 5,669,394 | A | 9/1997 | Bergery et al. | |
| 5,772,627 | A | 6/1998 | Acosta et al. | |
| 5,782,849 | A | 7/1998 | Miller | |
| 5,810,744 | A | 9/1998 | Chu et al. | |
| 5,911,701 | A | 6/1999 | Miller et al. | |
| 5,916,231 | A | 6/1999 | Bays | |
| 5,918,478 | A | 7/1999 | Bostic | |
| 5,997,560 | A | 12/1999 | Miller | |
| 6,017,354 | A | 1/2000 | Culp et al. | |
| 6,032,673 | A | 3/2000 | Savage et al. | |
| 6,086,544 | A | 7/2000 | Hibner et al. | |
| 6,144,016 | A * | 11/2000 | Garvin | A45C 11/20 206/550 |
| 6,152,871 | A | 11/2000 | Foley et al. | |
| 6,173,839 | B1 * | 1/2001 | Dieter | A45C 3/001 190/110 |
| 6,179,829 | B1 | 1/2001 | Bisch et al. | |
| 6,245,084 | B1 | 6/2001 | Mark et al. | |
| 6,258,111 | B1 | 7/2001 | Ross et al. | |
| 6,269,888 | B1 | 8/2001 | Schuda et al. | |
| 6,312,441 | B1 | 11/2001 | Deng | |
| 6,322,549 | B1 | 11/2001 | Eggers et al. | |
| 6,328,730 | B1 | 12/2001 | Harkrider, Jr. | |
| 6,402,701 | B1 | 6/2002 | Kaplan et al. | |
| 6,419,641 | B1 | 7/2002 | Mark et al. | |
| 6,491,699 | B1 | 12/2002 | Henderson et al. | |
| 6,592,530 | B1 | 7/2003 | Farhadi | |
| 6,609,020 | B2 | 8/2003 | Gill | |
| D479,455 | S | 9/2003 | Waldron | |
| 6,629,986 | B1 | 10/2003 | Ross et al. | |
| 6,659,998 | B2 | 12/2003 | DeHoogh et al. | |
| 7,019,234 | B1 | 3/2006 | Mezhinsky et al. | |
| 7,415,794 | B1 * | 8/2008 | Thompson | A01K 97/22 206/315.11 |
| 7,481,775 | B2 | 1/2009 | Weikel, Jr. et al. | |
| 7,572,236 | B2 | 8/2009 | Quick et al. | |
| 7,678,552 | B2 | 3/2010 | Kornblith | |
| 7,861,552 | B1 * | 1/2011 | Hughes | A45C 11/20 62/371 |
| 7,861,892 | B1 * | 1/2011 | White | B67D 1/06 222/108 |
| 2001/0037114 | A1 | 11/2001 | Dinger et al. | |
| 2002/0103496 | A1 | 8/2002 | Harper et al. | |
| 2003/0045811 | A1 | 3/2003 | Hinchliffe et al. | |
| 2003/0047434 | A1 | 3/2003 | Hanson et al. | |
| 2003/0073980 | A1 | 4/2003 | Finlay et al. | |
| 2003/0208136 | A1 | 11/2003 | Mark et al. | |
| 2004/0049217 | A1 | 3/2004 | Ross et al. | |
| 2005/0027210 | A1 | 2/2005 | Miller | |
| 2005/0035009 | A1 * | 2/2005 | Cuomo | B65D 71/0014 206/162 |
| 2005/0085798 | A1 | 4/2005 | Hofmann et al. | |
| 2005/0103607 | A1 | 5/2005 | Mezhinsky | |
| 2005/0154407 | A1 | 7/2005 | Simpson | |
| 2005/0277970 | A1 | 12/2005 | Norman et al. | |
| 2006/0115385 | A1 | 6/2006 | Jon Meyer | |
| 2006/0241343 | A1 | 10/2006 | Miller et al. | |
| 2007/0073226 | A1 | 3/2007 | Polidoro et al. | |
| 2007/0073326 | A1 | 3/2007 | Miller et al. | |
| 2007/0149977 | A1 | 6/2007 | Heavener | |
| 2007/0168051 | A1 * | 7/2007 | Bronnenberg et al. | 700/20 |
| 2007/0168851 | A1 * | 7/2007 | Hunt | 715/500 |
| 2007/0168852 | A1 * | 7/2007 | Erol et al. | 715/500.1 |
| 2007/0168862 | A1 * | 7/2007 | Hunt | 715/705 |
| 2007/0174758 | A1 * | 7/2007 | Ando et al. | 715/500.1 |
| 2007/0174917 | A1 * | 7/2007 | Guruswamy | 726/25 |
| 2007/0175238 | A1 * | 8/2007 | Norwood | A61J 1/165 62/457.3 |
| 2007/0270714 | A1 | 11/2007 | Cushner et al. | |
| 2008/0045964 | A1 | 2/2008 | Mishra | |
| 2008/0114387 | A1 | 5/2008 | Hertweck et al. | |
| 2008/0188767 | A1 | 8/2008 | Oaki et al. | |
| 2008/0234720 | A1 | 9/2008 | Chang et al. | |
| 2008/0243105 | A1 | 10/2008 | Horvath | |
| 2008/0249366 | A1 | 10/2008 | Gruber et al. | |
| 2008/0249553 | A1 | 10/2008 | Gruber et al. | |
| 2008/0262476 | A1 | 10/2008 | Krause et al. | |
| 2009/0112118 | A1 | 4/2009 | Quick, Jr. et al. | |
| 2009/0124975 | A1 | 5/2009 | Oliver et al. | |
| 2009/0131819 | A1 | 5/2009 | Ritchie et al. | |
| 2009/0171243 | A1 | 7/2009 | Hibner et al. | |
| 2009/0281477 | A1 | 11/2009 | Mikus et al. | |
| 2010/0152615 | A1 | 6/2010 | Mark et al. | |
| 2010/0292607 | A1 | 11/2010 | Moore et al. | |
| 2011/0056902 | A1 | 3/2011 | Cognard | |
| 2011/0190802 | A1 | 8/2011 | Mark et al. | |
| 2011/0281350 | A1 | 11/2011 | Schowalter et al. | |
| 2011/0282239 | A1 | 11/2011 | Conlon et al. | |
| 2011/0282372 | A1 | 11/2011 | Schowalter et al. | |
| 2011/0308271 | A1 | 12/2011 | Schryver | |

(56) References Cited

U.S. PATENT DOCUMENTS

| | | | |
|---|---|---|---|
| 2012/0157879 A1 | 6/2012 | Mark | |
| 2013/0068635 A1* | 3/2013 | Ralph | B65D 5/4608 206/139 |
| 2013/0211316 A1 | 8/2013 | Wilcox et al. | |

FOREIGN PATENT DOCUMENTS

| | | |
|---|---|---|
| EP | 0497520 A1 | 8/1992 |
| EP | 1201210 A1 | 5/2002 |
| EP | 1714617 A1 | 10/2006 |
| EP | 1815798 A1 | 8/2007 |
| EP | 1859742 A1 | 11/2007 |
| EP | 1915949 A1 | 4/2008 |
| WO | 9418894 A1 | 9/1994 |
| WO | 9613845 A1 | 5/1996 |
| WO | 9846147 A1 | 10/1998 |
| WO | 0022994 A1 | 4/2000 |
| WO | 0230303 A1 | 4/2002 |
| WO | 03045290 A1 | 6/2003 |
| WO | 2006123312 A1 | 11/2006 |
| WO | 2007002230 A1 | 1/2007 |
| WO | 2007005507 A2 | 1/2007 |
| WO | 2007047380 A2 | 4/2007 |
| WO | 2007062412 A2 | 5/2007 |
| WO | 2008023193 A2 | 2/2008 |
| WO | 2008058157 A2 | 5/2008 |
| WO | 2011146682 A1 | 11/2011 |

OTHER PUBLICATIONS

Health News, US Academic Health Center, University of Cincinnati, Jul. 9, 2008, "Brain Cancer 'Vaccine' May Help Prevent Recurrence."
Lesniak, ISSN 1473-7175, 2006, "Targeted therapy for malignant glioma: neural stem cells."
Human, www.curetoday.com, 2010, "Using personalized vaccines, researchers enlist the immune system to oust tumors."
Park, Alice, Time, Sep. 3, 2009, "A Shot at Cancer."
PCT International Search Report dated Jul. 9, 2013 from PCT/US2013/021938.
Smith & Nephew Dyonics, Inc., Feb. 1992, "Extending Your Athroscopic Reach."
Surgical Dynamics, 1993, "Endoflex Steerable Nucelotome for Endoscopic Microdisectomy."
Surgical Dynamics, 1992, "Nucleotome Flex II for Automated Percuaneoous Lumbar Discectomy."
Surgical Dynamics, 1992, "Surgical Technique Nucelotome Micro I for Automated Open Lumbar Discectomy."
Surgical Dynamics, 1993, "Micro II Bendable Nuceltome for Open Lumbar Discectomy."
J.M. Pirotte, M.D., et al., Clinical Studies Neurosurgery, vol. 64, No. 3, Mar. 2009, "Positron Emission Tomography-Guided Volumetric Resection of Supratentorial High-Grade Glimoas; A survival Analysis in 66 Consecutive Patients."
FDA U.S. Food and Drug Administration, Apr. 13, 2009, "New Device Approval—Arista TM AH Absorbable Hemostat—P050038."
Linesmaster Switch Corp., 2000, "Prescision Begins with a Linemaster Switch."
www.herga.com, Herga Electric Ltd., Apr. 30, 2009, "Heavy Duty Foot Potentionmeter."
Exair Corporation, Copyright 2009, "Vacuum Generators, How the E-Vac Works."
Martin L. Lazar, M.D., et al, Texas Neurological Institute at Dallas, vol. 3, No. 3, 1978, "An Automated Tumor Resection Device for Neurological Surgery."
Wang, et al., Journal of Clinical Engineer, Apr.-Jun. 1979, "Automated Tumor Extraction Device for Neurological Surgery."
PCT International Search Report for PCT/US2009/068313 dated Mar. 11, 2010.
PCT International Search Report for PCT/US2009/068225 dated Oct. 4, 2010.
Annex to form PCT/ISA/206 Communication Relating to the Results of the Partial International Search Report for PCT/US2009/068329 dated Mar. 5, 2010.
D.M. Keller, PhD., http://www.medscape.com/viewarticle/721786; May 13, 2010, "Paitents With Newly Diagnosed Gliobastoma Benefit Even From Less Than Total Resection."
PCT International Search Report for PCT/US2011/037092 dated Aug. 3, 2011.
PCT International Search Report for PCT/US2009/068329 dated Sep. 23, 2011.
Nakano, et al. Minim Invas Neurosurg, 2009, "Endoscopic Treatment for Deep-seated or Multiple Intraparenchymal Tumers; Technical Note."
Compton, Society of Surgical Oncology, 2009, "The Surgical Speciment is the Personalized Part of Personalized Cancer Medicine."
Schlomm, et al. European Urology 53, 2008; pp. 333-346, "Marked Gene Transcript Level Alterations Occur Early During Radical Prostatectomy."
Lin, et al., Journal of Clinical Oncology, vol. 24, No. 23, Aug. 10, 2006, "Influence of Surgical Manipulation on Prostate Geene Expression: Implications for Molecular Correlates of Treatment Effects and Disease Prognosis."
Spruessel, et al. Research Report, Center for Cancer Research at Israelitc Hospital, vol. 36, No. 6, 2004, "Tissue ischemia time affects gene and protein expression patterns within minutes following surgical tumor excision."
Dash, et al. American Journal of Pathology, vol. 161, No. 5, Nov. 2002, "Changes in Differential Gene Expression because of Warm Ischemia Time of Radical Prostatectomy Specimens."
Nishihara et al. J. Neurosurg 92: 1053-1055, 2000, "A transparent sheath of endoscopic surgery and its application in surigcal evacuation of spontaneous intracerbral hematomas."
Signoretti, et al. Review Clin Cancer Res, 2009; 14(12) Jun. 15, 2008, "Tissue-Based Research in Kidney Cancer: Current Challenges and Future Directions."
PCT International Search Report and Opinion for PCT/US2014/015006 dated Apr. 17, 2014.

\* cited by examiner

SYSTEM FOR COLLECTING AND PRESERVING TISSUE CORES

CROSS-REFERENCE TO RELATED APPLICATIONS

This application is a continuation-in-part of U.S. application Ser. No. 13/744,084, filed on Jan. 17, 2013, which application is a continuation-in-part of U.S. application Ser. No. 13/352,069, filed on Jan. 17, 2012, the contents of which are hereby incorporated by reference in their entirety.

TECHNICAL FIELD

The present disclosure relates to a system for collecting and preserving resected tissue cores.

BACKGROUND

Various abnormalities of body's bodily systems, including the neurological system, can cause severe health risks to patients afflicted by them. For example, in connection with a neurological system, abnormalities such as brain and spinal tumors, cysts, lesions, or neural hematomas can lead to deterioration in motor skills, nausea or vomiting, memory or communication problems, behavioral changes, headaches, or seizures. In certain cases, resection of abnormal tissue masses is required. However, given the various complexity and importance of various bodily functions where the abnormality may be found, such procedures may be extremely delicate and must be executed with great precision and care.

Various tissue removal systems are known or have been proposed for excising abnormal tissue from healthy tissue. However, many known tissue cutting devices suffer from an inability to precisely and atraumatically remove neurological tissue without causing damage to the tissue to be removed, as well as to the surrounding tissues which tissues to be removed are connected or attached to. Indeed, many prior art devices simply provide for a ripping or tearing action that removes diseased tissue away from the patient. Further, some prior art devices also do not provide for successive excision of tissue samples without removal of each tissue sample between each resection cycle.

Additionally, various tissue removal systems use ablative, disruptive or thermal energy, or a combination of these, which cause damage to the excised tissues, as well as the substrate and collateral tissue healthy tissues. Accordingly, these tissue removal mechanisms are not suitable for use when the integrity and viability of the tissue is desired to be maintained for subsequent use for the formulation of personalized medicine regimens. Nor do they allow for the capture and preservation of the resected tissue within a sterile environment. Additionally, the ablative energy that these devices generate also effects the collateral tissue, such as the substrate from which the tumor has been resected which causes the substrate to be damaged and less or even non-effective as a "receptor bed" for subsequent in-situ personalized medicine regimens.

Once diseased tissue is removed, traditionally patients are treated with a "one-size" fits all approach which typically includes a generic and heavy chemotherapy protocol regimen which is delivered to the entire body and designed to provide a balance between enough poison to kill the cancerous tissue without killing all of the healthy tissue. High doses and multiple exposures to radiation are also typically used and delivered by products such as the Gamma Knife and Cyber Knife. However, such invasive treatment regimens are often nothing more than a series of "experiments" on the patient in an effort to find an effective treatment plan. Accordingly, the patient must be monitored to ascertain the effectiveness of the generic therapeutic regimen and continuous modification and tweaking of the treatment regime is performed based upon the positive or negative results of each of the previous successes or failures while attempting to balance the sparing of healthy tissues and poisoning effect of the treatment process on the whole patient. Such a treatment regime effectively results in the patient being a guinea pig until an effective treatment regime is achieved to manage the disease or in most cases the patient dies from the disease. Unfortunately, in the case of brain cancers, the patient often succumbs to the disease before an effective treatment regime is achieved. Regardless of these heroic clinical efforts that are very biologically caustic to the patient, rarely are any of the current treatment paradigms curative. In fact, since patients diagnosed with brain cancers often do not typically live beyond 9-14 months after initial diagnosis of the disease, long term clinical implications of whole body chemo or target directed radiation therapy are unknown in these patients and may be detrimental if the patient lived long enough for the true impact to be understood.

However, currently evolving treatment protocols for certain diseases calls for patient specific targeted therapies, i.e., personalized medicine. Several forms of personalized medicine utilize diseased tissue from the patient, i.e., excised tissue, to obtain information about the general disease type, as well as the specific genetic and molecular make-up of the patient's specific disease. From this information, a targeted or personalized oncological treatment regime may be developed that requires the use of the patient's own tissue, which is cultured and used to create a patient specific "cocktail" which may then be delivered back into the patient as a tailored specific therapy regime for that patient.

For effective treatment protocols to be developed, the tissue resected from the patient must be removed, collected and transported in a way that does not compromise the biological integrity or efficacy of the tissue so that it may be not only analyzed by pathology but so further oncological processing may be performed on the tissue so that a patient specific therapeutic cocktail may be created. Traditionally, pathologists only receive limited quality tissue samples and/or limited amounts of tissue due to tissue being damaged during the removal process, or that only a small amount of tissue was able to be retrieved. Tissues for pathological evaluation usage are not required to be maintained in a sterile or aseptic format once removed from within a sterile field, nor was biological integrity or efficacy required. The only requirements were that the tissue not be crushed beyond recognition and not dehydrated. However, for certain types of personalized medicines to be effectively created, there must be sufficient tissue harvested from the tumor and available to an oncological lab (vs. a pathology lab), it must be biologically active and intact, while maintained in a sterile or aseptic environment so that it is not contaminated by foreign matter or biological elements such as bacteria, fungus, etc. This uncompromised environment allows for the effective subsequent culturing of tissue thus allowing the creation of a specific patient therapeutic regimen that enables the creation of personalized medicine therapies. More specifically, there must be an adequate volume of tissue harvested from the tumor, maintained in a sterile or aseptic environment that allows for the resected tissue to be divided for further use as tissue that may be effectively cultured. In some cases it is preferable that the resected tissue be presented to pathology or for oncological processing in predefined consistent sized samples. This offers the opportunity for less manual handling at the point of lab processing of the tissue and therefore less inadvertent physical to the tissue architecture damage which further impacts the true yield of tissue available for pathological or oncological use. Another benefit is that it provides pathology more discreet units for evaluation rather than an en-bloc presentation to pathology (where the en-bloc tissue may only be divided up a few times) of tissue thereby enabling a more complete evaluation of more samples which may produce a more effective evaluation from more of the tumor material. In the case of oncological processing for the creation of patient specific chemotherapy, the tissue samples are first analyzed by pathological means for the determination of specific types of tumor information. Once determined, the tissue, which has been maintained in a sterile or aseptic environment, is then plated for culturing and a variety of different "chemical cocktails" of varying degrees of intensity and composition may be applied to determine which "cocktail" provides the most effective "kill" to the cancer and the least amount of damage to healthy tissue. This procedure is typically referred to as "targeted chemotherapy." An example of the screening of such candidate therapeutic or chemotherapeutic agents for efficacy as to a specific patient is described in U.S. Pat. No. 7,678,552, which is assigned to Precision Therapeutics, Inc. (Pittsburgh, Pa.), the contents of which are incorporated herein by reference in its entirety.

Another emerging therapy that has been developed is immunotherapy treatments. Immunotherapy treatments utilize the immune system of the patient to fight disease. Generally, such treatments involve harvesting antigen presenting tissue and/or cells from the patient and incubating the tissue/cells containing the antigen of the specific diseased being targeted. The antigen presenting cells swallow up the disease antigen and present the antigen on its surface. The antigen presenting cells are then placed in-situ back into the patient to boost and/or function to train the body's own T-cells to attack any cells that display the disease antigen. Additionally, there are other forms of treatment regimes that use the patient's own tumor cells and tissues, which have been cultured to create specific cocktails to be delivered in-situ which are viral based vectors. An example of one company employing such a technique is Tocagen, Inc. (San Diego, Calif.).

The current challenge for prior art tissue cutting devices is the ability to achieve a safe and effective Gross Total Resection (GTR) or near GTR, to provide the lab with intact segments (biopsy quality tissue, not just cells or macerated tissue) of patient's tissue with little to no crush artifact. Consistency in the "bite" size of the resected tissue is also a challenge. Same or near same sized dimensionally resected tissue bites would minimize post processing handling for oncological use and culturing. A slurry of cells or macerated tissue is not very useful for pathology and unacceptable for an effective oncologically based treatment protocol when tissue culturing is required, current resection techniques and devices do not effectively deliver what is required.

The tissue resected by the surgeon and analyzed by the pathologist is the source of crucial information and that same tissue is used to create from the patient's own tissues the appropriately effective treatment protocol to be used. Indeed, the surgically resected tissue possesses the molecular information needed to define the specific molecular characteristics of the patient's tumor, the specific therapies to which the tumor would be expected to respond, and even the specific risks of adverse reactions to given therapies predicted by the patient's genetic make-up.

However, safeguarding the molecular integrity and efficacy of the resected tissue while in the operating room and during transport to the laboratory, is currently a challenge. Tissue samples react to physiological stress. For example, once successfully resected, the specimen may spend varying amounts of time in a biologically unfriendly environment such as at room temperature in the surgical suite and/or holding unit, allowed to be exposed to atmosphere, allowed to dry out, placed in a non-sterile/non-aseptic environment, etc. before being delivered to the laboratory. Temperature may alter the molecular composition and quality of the tissue samples. Similarly, other physiological stress may also detrimentally impact the tissue samples, such as perfusion and oxygenation.

Immunotherapy treatments require biologically active tissue that are tissue blocks, not just individual cells. In fact, it is known that individual cells from diseased tissue respond and act biologically differently than do "colonies" (blocks) of tissue when subjected or exposed to therapeutic agents. Thus tissue must be resected without crush artifact, ablative destruction of the cell walls or thermal damage, such as char, for the benefit of pathological evaluation and for use in personalized medicine oncological therapies. Additionally, it is not just the viability of the resected tissue that must be considered but also the substrate from which the resected tissue has been harvested that also must be respected and not damaged so that it may act as an effective receptor bed for personalized medicine therapeutic regimens that require in-situ placement of the regimen. Moreover, these treatment regimens also require a minimum volume of tissue for effective use. Finally, the tissue that is resected, collected, transported, must be preserved in an aseptic or preferably a sterile environment which precludes dehydration, contamination or compromise so it may remain biologically active and efficacious so that it may be cultured (i.e., living and biologically active tissue that is not compromised with contamination) for additional/advanced pathology based tissue testing and the needs of further processing to accomplish the needs of neuro-oncology and neuro-immunology for targeted therapies such as chemo, viral and other immune therapies for the achievement of personalized medicine.

Thus, a need has arisen for a system that utilizes a tissue cutting device that addresses the foregoing issues, as well as a system that provides for effective transport of resected tissue while minimizing, if not eliminating detrimental stress on the tissue samples.

BRIEF DESCRIPTION OF THE DRAWINGS

Embodiments of the present disclosure will now be described by way of example in greater detail with reference to the attached figures, in which.

DETAILED DESCRIPTION

Figure 1:
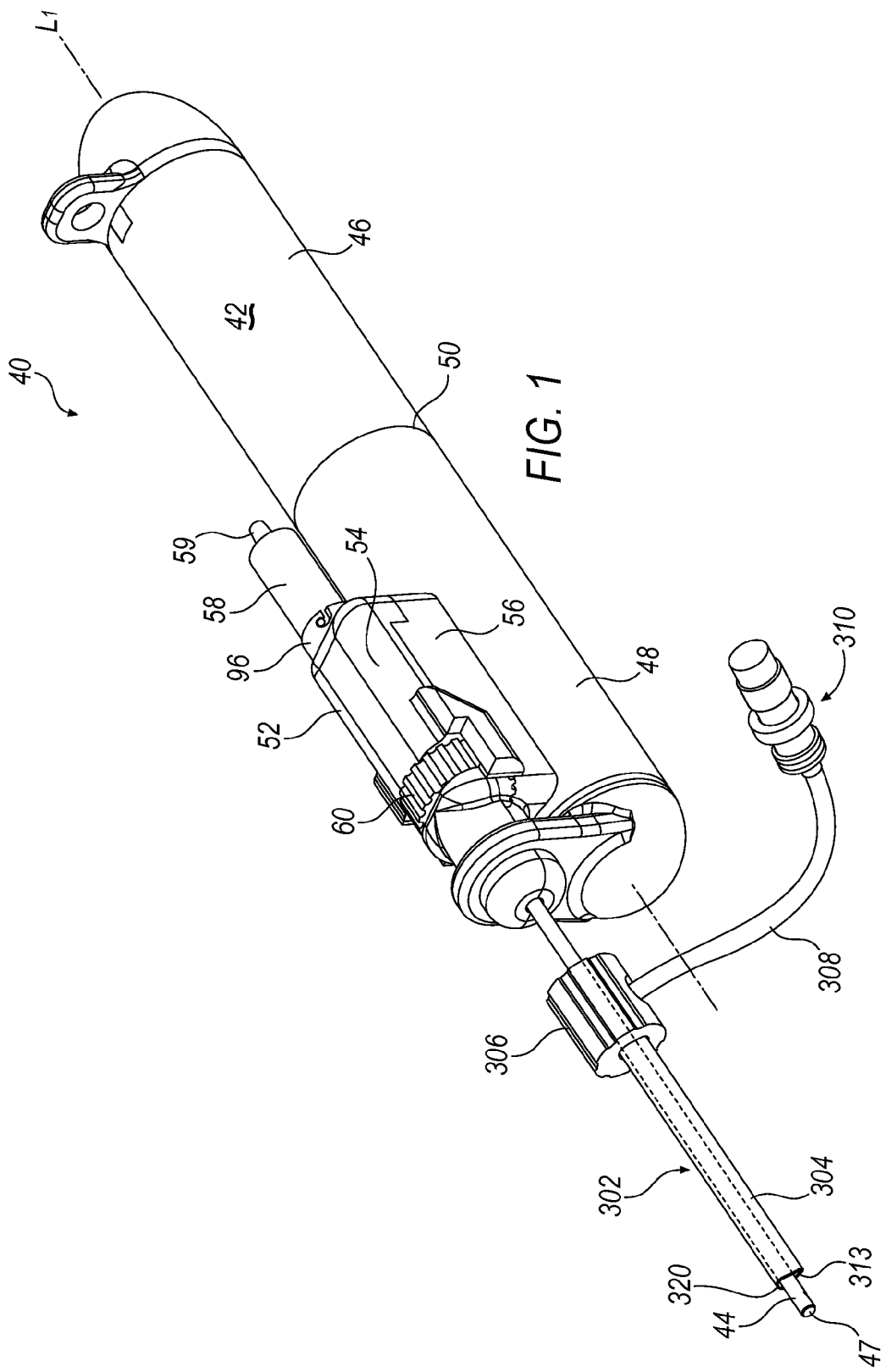
FIG. 1 is a perspective view of an exemplary tissue cutting system.

Referring now to the discussion that follows and also to the drawings, illustrative approaches to the disclosed systems and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein is an exemplary arrangement for a tissue cutting device that is suited for surgical applications, as well as a cooling system that may be used to preserve tissue cores taken using suitable tissue cutting devices. While described herein in connection with neurosurgical applications such as the removal of spine and brain tissue, it is understood that the disclosure herein is applicable to other surgical applications and treatment protocols. As described herein, the devices may be configured with an optional fluid supply sleeve that may be selectively disposed on an outer cannula of the tissue cutting device and selectively positionable along the length of the outer cannula. As a result, the fluid supply sleeve can be configured to supply fluids such as irrigants, hemostatic agents, pharmacological therapeutics and/or tissue sealants to a surgical site, and adjacent a tissue cutting opening of the surgical device. The fluid supply sleeve may also be used to selectively adjust the area of the outer cannula aperture through which the aspiration is delivered through to the tissue.

Methods and system for preserving tissue samples for use in development of personalized medicine regimens are also disclosed. The systems disclosed herein permit transport of excised tissue samples, while protecting the tissue samples from, for example, adverse environmental stress. Moreover, the tissue collection systems described herein also provide for preserving excised tissue samples by maintaining an effective temperature for the tissue samples collected.

An optional tissue preservation system is also described herein that may be used with the cooling systems disclosed herein, or may be used as a standalone system. The tissue preservation system may be used to provide nutrients for a biologically friendly, tissue efficacy prolonging environment to the resected tissue, as well as delivering a cooling bath to tissue samples disposed within a tissue collector.

Referring to FIG. 1, a tissue cutting device 40 includes a handpiece 42 and an outer cannula 44. In one exemplary embodiment, handpiece 42 is generally cylindrical in shape and is preferably sized and shaped to be grasped with a single hand. However, handpiece 42 is not limited to any particular shape and may also be contoured, and optionally include finger grips (not shown). Handpiece 42 includes a lower housing 50 which comprises a proximal section 46 and distal section 48. Lower housing 50 comprises a proximal-most housing portion (not shown) that is connected to a motor housing (not shown), and a cam housing (not shown) that is connected to the motor housing. Details of the motor housing and cam housing may be found in U.S. Ser. No. 13/352,069, the contents of which are incorporated by reference in its entirety.

An upper housing 52 is also provided. A tissue collector 58 may be operatively connected to upper housing 52. In another alternative arrangement (best seen in FIG. 2A) tissue collector 58 is connected to upper housing 52 via a length of tubing 151a that extends therefrom, as will be discussed in further detail below. A rotation dial 60 for rotating the outer cannula 44 with respect to handpiece 42 is also mounted to upper housing 52.

Outer cannula 44 includes an open proximal end 45 and distal end (not shown) that extends into upper housing 52. Tissue cutting device 40 further comprises an inner cannula (not shown) which is partially disposed in a lumen of outer cannula 44. Details of outer cannula 44 and the inner cannula may be found in U.S. Ser. No. 13/352,069. The inner cannula is configured to reciprocate within the outer cannula lumen and to cut tissue samples entering outer cannula 44 via an outer cannula distal opening 49 (see FIG. 2A), without crush artifact or thermal damage. A distal end of the inner cannula is configured to cut tissue, and in exemplary embodiments is capable of cutting neurological system tissues such as those from the brain or spine. In one exemplary embodiment, the inner cannula distal end is beveled in a radially inward direction to create a sharp circular tip and facilitate tissue cutting. The inner cannula may also include a hinge that allows a cutting section to pivot about the hinge as the inner cannula reciprocates within outer cannula 44. Details of the hinge may also be found in U.S. Ser. No. 13/352,069.

Outer cannula 44 is not translatable with respect to handpiece 42 such that its position with respect to handpiece 42 along the direction of the longitudinal axis of handpiece 42 remains fixed. The exemplary fluid supply sleeve 302 (FIG. 1) may be selectively attachable to outer cannula 44. Fluid supply sleeve 302 is configured to allow fluids to be provided proximate a surgical site and/or adjacent distal opening 49. In one exemplary configuration, fluid supply sleeve 302 has a proximal hub 306 and a distal end 320. An outer cannula opening (not shown) is provided at the proximal end of fluid supply sleeve 302. An elongated channel section 304 is connected to proximal hub 306 and projects distally away from it. Distal end 320 of fluid supply sleeve 302 is the distal end of the elongated channel section 304. In FIG. 1, fluid supply sleeve 302 is shown in an installed condition on outer cannula 44. In the depicted installed condition, fluid supply sleeve 302 is selectively positionable along the length of outer cannula 44.

A variety of different fluids may be delivered to a target tissue or proximate to the target tissue. In one example, irrigants such as saline are used to hydrate tissue at the surgical site, as well as to provide hydration of the tissue while the excised tissue sample is being aspirated. Further, in other exemplary arrangements, the fluid supply operatively connected to the fluid supply sleeve 302 may include a nutrient-rich solution configured to maintain the viability of the samples excised by device 40. In yet another example, a temperature controlled fluid may be provided through fluid supply sleeve 302 designed to preserve excised tissue being aspirated through device 40. Saline elevated in temperature may also function as a hemostatic agent to initiate a "clotting cascade" which ultimately leads to the clotting of ruptured blood vessels in tumors or other tissues at the surgical site. Other hemostatic agents, sealants, and/or tissue adhesives may also be delivered to a surgical site via fluid supply channel 312. Examples include liquid embolic systems such as Neucrylate, a cyanoacrylate monomer derivative supplied by Valor Medical. Neurcrylate is delivered as a liquid and forms a spongy, solid material upon contacting blood. Another example of a suitable hemostatic agent is supplied by Medafor, Inc. under the name Arista AH Absorbable Hemostat. Arista AH functions as a molecular filter by separating serum from cellular constituents. It absorbs water from the blood and forms a gel matrix that slows blood flow and serves to enhance clotting.

Fibrin sealants may also be delivered to a surgical site via fluid supply channel 312. One suitable hemostatic matrix sealant is FloSeal®, a fibrin sealant comprising human thrombin which is supplied by Baxter Hyland Immuno. Another suitable sealant is Tisseel, a VH Fibrin Sealant comprising human thrombin, human fibrinogen, and bovine aprotinin. Certain sealants may comprise two or more fluid components that are mixed at or near the site of delivery. In such cases, the at least one fluid supply channel 312 preferably comprises two or more fluid supply channels that contain the respective two or more fluid components which are mixed at open distal end 313 of fluid supply channel 312. For fluids that are viscous and/or or gel-like in nature, a source of pressure such as a pump is preferably provided to deliver them through fluid supply channel 312 to the tissue.

Synthetic sealing agents may also be delivered via fluid supply channel 312. One such example is CoSeal, a hydrogel comprising 2 polyethylene glycol polymers supplied by Baxter. The 2 polymers are preferably delivered via two separate fluid delivery channels and chemically bond to one another on mixing to form a mechanical barrier that slows bleeding. Another suitable synthetic seal is Duraseal, which is supplied by Confluent Surgical. Duraseal comprises a polyethylene glycol polymer ester solution that is mixed at the point of delivery with a trilysine amine solution. Thus, fluid supply sleeve 302 is preferably provided with two fluid delivery channels to facilitate mixing of the two solutions at the point of delivery.

Tissue cutting device 40 employs a motor that is positioned with lower housing 50 to facilitation reciprocation of the inner cannula within outer cannula 44. The motor may be selected to have a rotational speed that allows the inner cannula to reciprocate from a first proximal position to a second distal position and back to the first proximal position at a rate of at least about 1,000 reciprocations per minute. Reciprocation rates of at least about 1,200 reciprocations/minute are more preferred, and reciprocation rates of at least about 1,500 reciprocations/minute are even more preferred. Reciprocation rates of less than about 2,500 reciprocations/minute are preferred. Reciprocation rates of less than about 2,000 are more preferred, and reciprocation rates of less than about 1,800 reciprocations/minute are even more preferred. The appropriate rates of reciprocation of device 40 allow tissue to be severed into "snippets" which are relatively smaller than "slug" tissue samples obtained by many prior devices. The smaller sized "snippet" format permits use of the excised tissue samples for pathology or diagnostic purposes without necessarily requiring further manual or mechanical reduction of sample sizes. The smaller size samples provides a benefit as handling of tissue samples to reduce the size of excised tissue samples may expose the tissue to environmental factors that may degrade or otherwise compromise the biological integrity of the tissue samples. For example, in reducing the size of the excised tissue samples, bacteria may be inadvertently introduced. In the exemplary configuration, as shown in U.S. Ser. No. 13/352,069, as the reciprocation of the tissue cutting device continues, a continuum of severed tissue snippets is obtained.

Tissue cutting device 40 is particularly well suited for use in cutting tough tissues such as spinal and brain tissues. Outer cannula 44 and the inner cannula comprise materials that are generally rigid, such as rigid plastics or metal. In one preferred implementation, both cannulae comprise stainless steel, and more preferably, 304SS typically used in medical grade instruments.

Outer cannula opening 49 may have a number of shapes. In certain examples, when outer cannula opening 49 is viewed in plan, it has a shape that is generally square, rectangular, trapezoidal, ovular, or in the shape of the letter "D." In certain other exemplary implementations, outer cannula opening 49 is configured to direct tissue so that it may be compressed as the inner cannula translates in the distal direction.

Figure 2A:
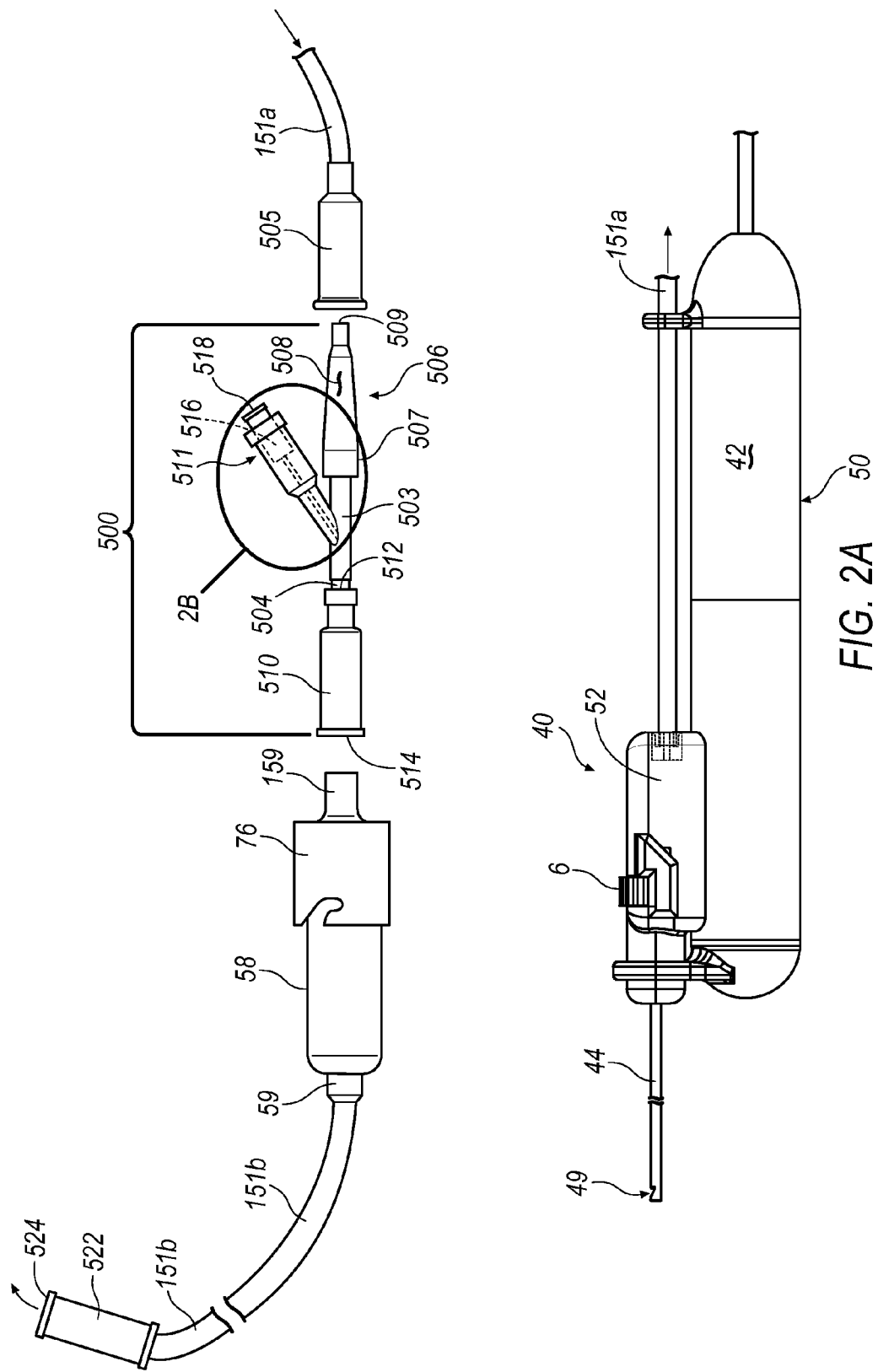
FIG. 2A is an embodiment of a tissue cutting system with a remote tissue collector and an optional tissue preservation system.

Tissue cutting device 40 aspirates tissue samples received in the inner cannula to cause the tissue samples to move in the proximal direction along the length of the inner cannula. In embodiments wherein tissue collection is desired, device 40 includes a tissue collector 58 into which aspirated tissue samples are deposited during a tissue cutting procedure. Tissue collector 58 may be located remotely from handpiece 42 and outside the sterile field during a tissue cutting operation as shown in FIG. 2A. However, in certain embodiments, as best seen in the examples of FIG. 1, tissue collector 58 is removably connected directly to handpiece 42 within the sterile field. However, it is understood that tissue collector 58 may also be remotely connected to handpiece 42, while in the sterile field, as well. In either embodiment, a fluid collection canister (not shown) may be located between tissue collector 58 and a source of vacuum (such as vacuum generator) to protect the vacuum generating apparatus from becoming contaminated or damaged by aspirated fluids, as disclosed in U.S. Ser. No. 13/352,069.

In other embodiments, a tissue collector may be omitted and the fluid collection canister may be provided to collect both aspirated fluid and tissue. Further, the fluid collection canister may also be provided with a tissue preservation solution configured to maintain the tissue samples viability and biological integrity, such as, for example, a nutrient rich solution designed to maintain the tissue samples in an aseptic environment.

Figure 2B:
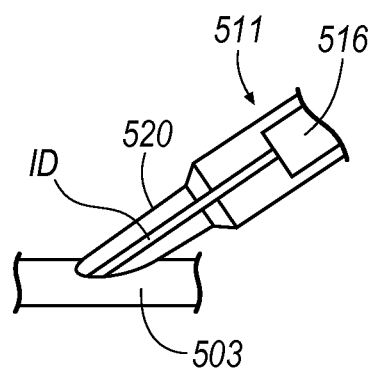
FIG. 2B is a blow-up of encircled area 2B in FIG. 2A, which is a portion of the tissue preservation system of FIG. 2A.
Figure 3:
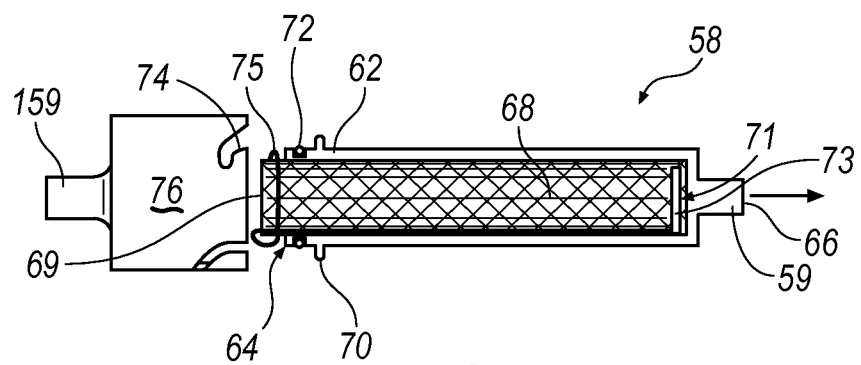
FIG. 3 is a partial cross-sectional view of a tissue collector assembly.
Figure 4:
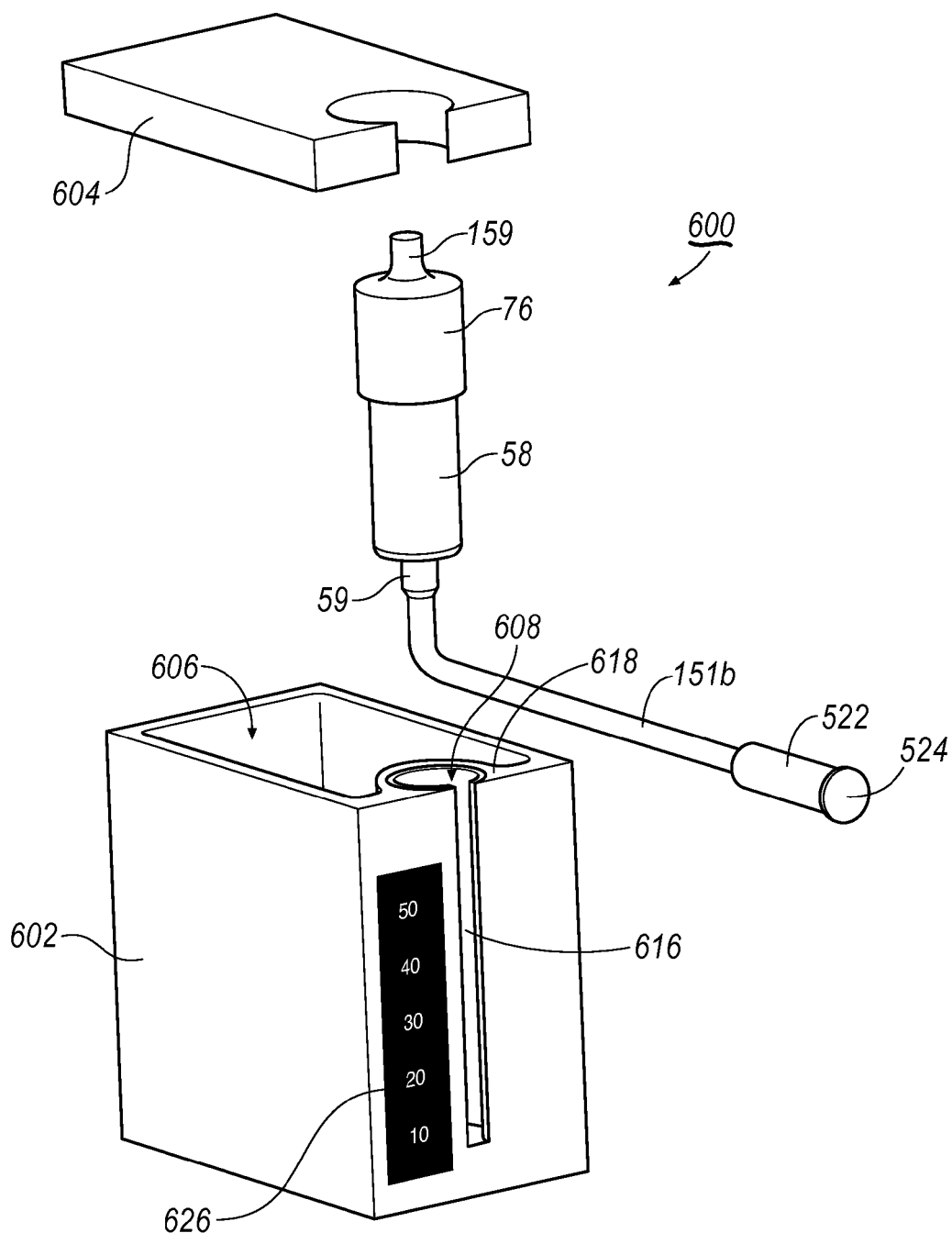
FIG. 4 is an exploded view of an exemplary temperature controlled system for use with a tissue collector.
Figure 5:
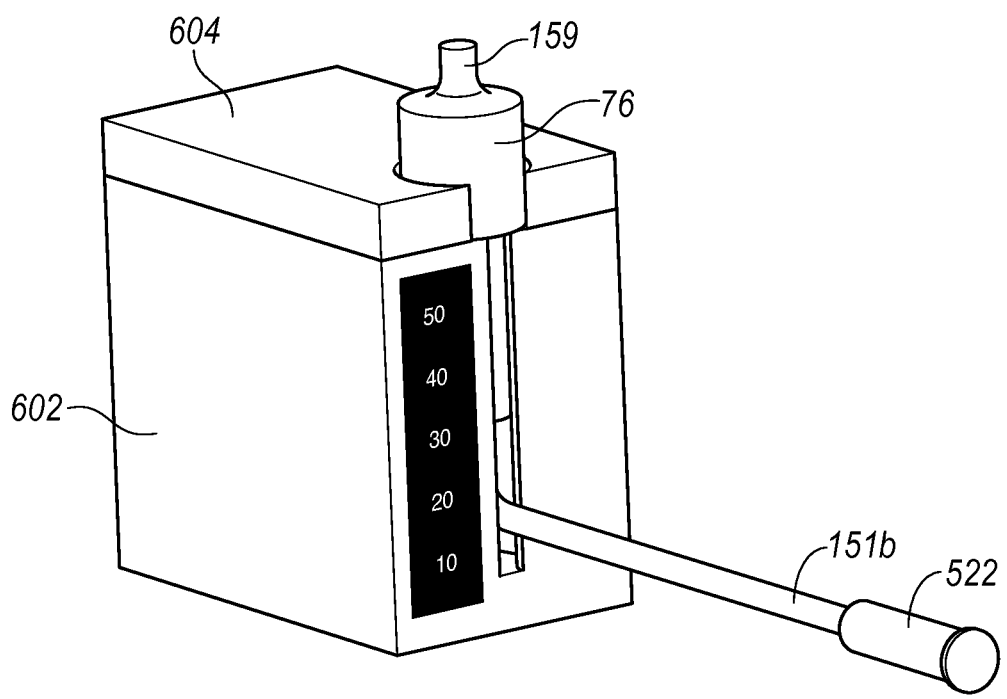
FIG. 5 is a perspective view of the temperature controlled system of FIG. 4 with the tissue collector positioned therein.
Figure 6:
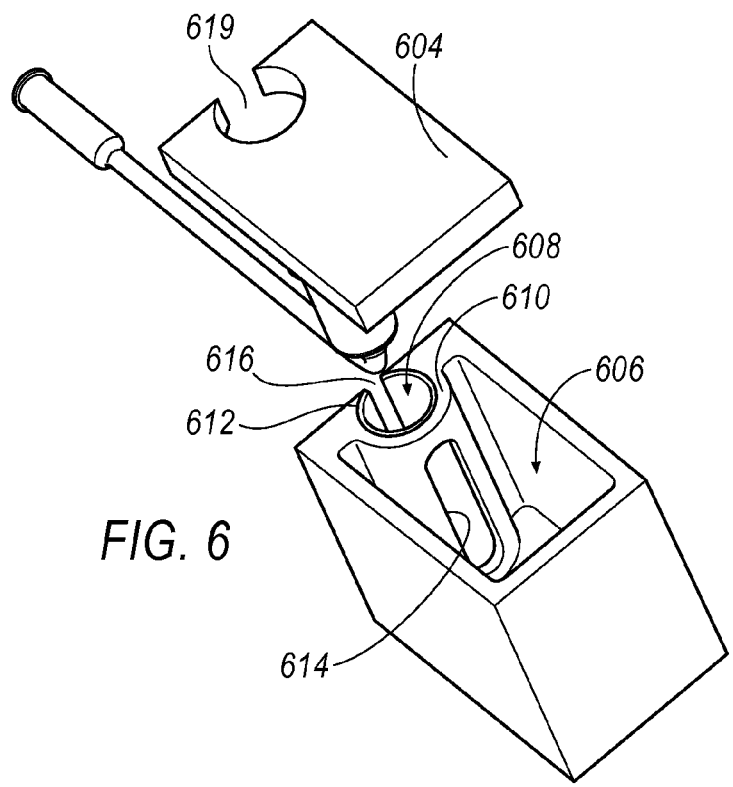
FIG. 6 is a partial exploded perspective view looking into the temperature controlled system of FIG. 4.
Figure 7:
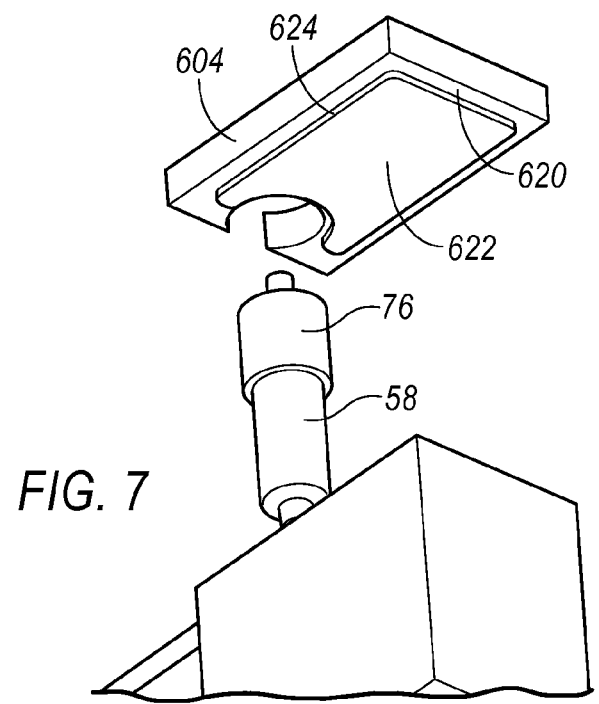
FIG. 7 is a partial exploded perspective view looking at the bottom surface of an exemplary lid that may be used with the temperature controlled system of FIG. 4.

Referring to FIGS. 1-3, tissue collector 58 may be operably connected to upper housing 52, either directly or remotely via tubing 151a to receive the aspirated tissue samples. Tissue collector 58 is a generally cylindrical, hollow body with an interior volume that is in fluid communication with the inner cannula lumen and a source of vacuum (not shown). Tissue collector 58 is configured to be removably secured to housing connector 96 (best seen in FIG. 1) for those emodiments where the tissue collector 58 is secured directly to housing 52. This configuration allows for the periodic removal of collected tissue samples, including while in the sterile field. As will be explained below, where tissue collector 58 is remotely connected to housing 52, tissue collector 58 operably engages with a cap member 76. Tissue collector 58 is preferably secured to upper housing 52 in a manner that provides a substantially leak-proof vacuum seal to maintain consistent aspiration of severed tissue samples. A vacuum hose fitting 59 is formed on the proximal end of tissue collector 58 and is in fluid communication with the interior of tissue collector 58 and with a vacuum generator, as will be discussed below.

As best seen in FIG. 3, the tissue collector 58 includes a generally hollow body portion 62 that has a first open end 64 and a second substantially closed end 66. Second end 66 defines a small opening therein, and permits vacuum to be delivered through body portion 62, as well as permit fluid to be evacuated from tissue collector 58. Vacuum hose fitting 59 is disposed around the small opening of second end 66.

To assist in removing tissue samples from tissue collector 58, a tissue filter 68 is removably disposed within body portion 62 through first open end 64. Tissue filter 68 is configured with a mesh-like body that is designed to retain tissue samples, but permits fluids to exit through the mesh-like body and be aspirated from tissue collector 58.

To assist in removal of tissue samples from tissue filter 68, in one exemplary arrangement, tissue filter 68 is configured with scoop 71 that is disposed within tissue filter 68. Scoop 71 includes an end portion 73 that is configured to be approximately the same size and shape as the interior of tissue filter 68. End portion 78 is secured to a pull member 75 that loops around an outer surface of tissue filter 68. To remove tissue samples from filter 68, pull member 75 is configured to be pulled away from tissue filter 68, which causes scoop 71 to advance toward an open end 69 of tissue filter 68 so as to move tissue samples to the opening of tissue filter 68. In another exemplary configuration, tissue filter 68 may be configured with a hinge member as shown and described in U.S. Pat. No. 7,556,622, the contents of which are incorporated herein by reference.

Adjacent first open end 64 are lug members 70 and a sealing groove into which a sealing member 72 may be disposed. Lug members 70 are configured to be selectively received within receiving grooves 74 of a cap member 76 in a bayonet-style engagement. Cap member 76 is open on one end and substantially closed on another. A hose fitting 159 extends from cap member 76 that may selectively attach to a vacuum line.

To enable the severed tissue samples to be used for personalized medicine regimens, viability and integrity of the tissue samples must be maintained after removal of the tissue samples from the patient, and during the collection and transport of the tissue samples to the oncological laboratory. More specifically, the tissue samples must be kept biologically active and intact, while maintained in a sterile or aseptic environment to permit the tissue to be cultured. Further, physiologic stress on the tissue samples must be minimized so as not to adversely impact the samples.

In exemplary arrangement, which may be used by itself, or with temperature controlled systems 600 and 700, to be described below in further detail, to provide nutrients for a biologically friendly, tissue efficacy prolonging environment to the resected tissue, referring to FIG. 2A, a preservation and tissue maintaining adapter system 500 may be positioned between tissue collector 58 and device 40. In one exemplary arrangement, preservation adapter system 500 is configured with a Y-shaped connector containing a valve element.

More specifically, preservation adapter system 500 includes a first connector element 502 (best seen in FIG. 2A) connected to a first end of a body portion 503 and a second connector element 504 connected to an opposite end of body portion 503. In one exemplary configuration, first connector element may 502 may be configured to be received directly within an open proximal end of a fitting 505 connected to vacuum line 151a. In the exemplary configuration shown in FIG. 2A, an adapter element 506 connects the first connector element to fitting 505. In the exemplary configuration shown in FIG. 2A, adapter element 506 includes a first end 507 that is sized to receive, or otherwise connect to, the first connector element 502 in any suitable manner, including, but not limited to, a threaded engagement. Adapter element 506 may be configured with an elongated body 508 that terminates in a second end 509. Second end 509 is configured to be received within an open proximal end of fitting 505. In the exemplary configuration shown in FIG. 2A, body 508 tapers from first end 507 to second end 509.

Second connector element 504 is configured to secure preservation adapter system 500 to tissue collector 58 via cap member 76. In one exemplary configuration, second connector end 504 is configured to be received within, or otherwise connected to a fitting 510. More specifically, fitting 510 includes a first end 512 that receives second connector element 504, in any suitable manner, and a second end 514 that is configured to connect to hose fitting 159.

A needless syringe port 511 intersects body portion 503. Port 511 may be configured with a valve element 516 (shown in phantom) in communication with an opening 518 to port 511. Port 511 (and valve element 516) allow for introduction of solution to the tissue samples, while the tissue samples being deposited into tissue collector 58.

More specifically, preservation adapter system 500 may be configured to permit a controlled flow rate of a solution into the tissue collector 58, and hence to permit the tissue samples to be bathed in this solution. In one exemplary configuration, regulation of the quantity of fluid flow that is delivered to the tissue within tissue collector 58 may be defined by an internal diameter ID of a connector neck 520, that is smaller than the flow channel defined by body portion 503. The fluid flow may also be controlled and/or restricted by an internal orifice (not shown), positioned within neck 520, whereby the orifice has a diameter that is smaller than the internal diameter ID of neck 520. Additionally, valve element 516, which may be provided as either fixed or adjustable valve, can be provided in-line with the internal diameter ID of neck 520. Alternatively, a flow control valve (adjustable or fixed) may be provided in a supply line that serves as a connection between port 518 and a source of preservation solution.

In operation, to assist in preservation of tissue samples, preservation adapter system 500 may be used to introduce a nutrient rich or preservative solution into the artificial environment of tissue collector 58 to keep the tissue samples properly hydrated and nourished. In one exemplary arrangement, the fluid may be one of a tissue efficacy prolonging or boosting solution, a pre-processing solution for the preparation of culturing, a viral inoculation solution, a tissue preservation solution, or a thrombolytic agent. In another configuration, the fluid may be configured to initiate the beginning of cellular disassociation. It is also contemplated that the fluid may be a combination of any of the foregoing. A source of suitable solution may be fluidly connected to port 518 via suitable fitting and fluid supply such that vacuum may draw the solution through valve 516 and internal diameter ID and into body 503, via vacuum line 151B. In another exemplary configuration, the solution introduced by preservation adapter system 500 may be chilled to further assist in preserving tissue for future oncological use, but may be metered (by valve 516 and/or internal diameter ID/orifice) to provide a specific flow rate for the solution being introduced.

Suitable fluids designed to maintain and/or preserve tissue samples for further use may be introduced via syringe. Alternatively, as suggested above, a solution may be automatically drawn into port 518 via the vacuum pressure supplied to tissue collector 58 via vacuum line 151B, thereby providing a consistent solution to the tissue samples.

As shown in FIG. 2A, vacuum line 151*b* is attached to tissue collector 58. In one exemplary arrangement, a connector element 522 having an open proximal end 524 is attached to vacuum line 151*b*. Connector element 522 is configured to be fluidly connected to an inlet (not shown) of a collection canister to deposit bodily fluids and excess solution within the canister. Details of this arrangement may be found in U.S. Ser. No. 13/352,069. However, to allow transport of excised tissue samples, while maintaining the aseptic environment in which the excised tissue samples are stored, connector element 522 is configured to be selectively released from the inlet of the collection canister and looped around and re-attached to hose fitting 159. More specifically, hose fitting 159 is received within open proximal end 524, thereby creating a closed environment system that may be easily transported, without contacting or contaminating the tissue samples. More specifically, this configuration provides an internally sterile/aseptic environment that is ingress proof from atmosphere conditions, while also being compliant with OSHA biohazard requirements such that tissue collector 58 provides a fluid/leak proof chamber that is safe for the staff handling tissue collector 58, as well as being compliant for easy transportation.

As discussed above, it is important to minimize physiologic stress on tissue samples to preserve the validity and integrity of the tissue samples after excision. An exemplary embodiment of a temperature controlled system 600 is shown in FIGS. 4-7 to assist in achieving the goal. Temperature controlled system 600 may be used with the tissue cutting 40, as well as with preservation adapter system 500. However, it is expressly contemplated that temperature controlled system 600 may be used independently, without preservation adapter system 500 or with other tissue cutting devices.

Temperature controlled system 600 is utilized in those embodiments where tissue collector 58 is remotely connected to tissue resection device 40, as shown in FIG. 2, for example. Cooling system 600 includes a base member 602 and a lid 604. Base member 602 is configured as an insulated member that comprises a reservoir 606 and a tissue collector chamber 608. In one exemplary arrangement, tissue collector chamber 608 is defined by a contoured wall 610, integral with base member 602. However, it is understood that a separate sleeve member may be positioned within base member 602 to serve as a tissue collector chamber 608.

In one exemplary arrangement, a sleeve member 612 lines and is in contact with the outside of tissue collector chamber 608. Sleeve member 612 is constructed of a thermally conductive material, as will be explained in further detail below. The wall member that defines tissue collector chamber 608 further comprises an opening 614 (best shown in FIG. 6) that is in communication with reservoir 606. As will be explained further below, opening 614 also permits sleeve member 612 to directly contact any material that is contained within reservoir 606.

Base member 602 further comprises a narrow slit 616. Slit 616 extends from a top edge 618 of base member 602 to a bottom of tissue collector chamber 608. Slit 616 is sized to permit vacuum line 151*b* to pass through.

Lid 604 is sized to fit over base member 602 to retain materials positioned within reservoir 606, as well as to retain tissue collector 58 therein. Lid 604 further includes an opening 619 through which hose fitting 59*b* extends, when tissue collector 58 is positioned within tissue collection chamber 608. In one embodiment, a bottom surface 620 of lip 604 is provided with a projecting element 622 configured to fit within an opening of reservoir 606. A seal member (not shown) may be provided around a peripheral edge 624 of projecting element 622 to provide a water tight/sealed chamber. An external latching member may be provided to secure lid 604 to base member 602.

In operation, lid 604 is removed from base member 602. Reservoir 606 is filled with a suitable temperature controlling medium. For example, one temperature controlling medium includes a refrigerant (i.e., ice or other suitable liquid). Tissue collector 58 is positioned within tissue collector chamber 608, with vacuum line 151*b* extending out of slit 616. Lid 604 is then attached to base member 602, sealing reservoir 606. Lid 604 may be insulative to maintain the temperature of the materials within reservoir 606. Hose fitting 59*b* extends upwardly from lid 604 and is connected via vacuum line 151*a* to tissue resection device 40.

Due to the thermo-conductivity of sleeve 612, and because sleeve 612 is in direct communication with the temperature controlling medium positioned within reservoir 606, tissue collector 58 (and hence any tissue samples positioned therein) are kept at a suitable temperature to maintain tissue viability. Moreover, since reservoir 606 for the temperature controlling medium is insulated and water tight, suitable temperature controlling mediums may be directly placed into reservoir 606 and replenished as necessary during use. Further, in another exemplary configuration, base member 602 may be provided with an external temperature gauge 626. Temperature gauge 626 is configured to be in communication with reservoir 606 or in communication with sleeve 612 thereby providing an indication when additional refrigerant may be needed and of the thermal status of the contents within tissue collector 58. For example, in one exemplary configuration an end portion of sleeve 612 is extended along a portion of base member 602. An opening (not shown) is provided through a surface of base member 602 and temperature gauge 626 is positioned over the opening and in contact with the extended portion of sleeve 612. Accordingly, the temperature of tissue collector 58 is communicated to temperature gauge 626.

In another exemplary arrangement, an opening (not shown) is formed in the inside surface of base member 602, similar to opening 614. Temperature gauge 626 is positioned within base member 602 over the opening so as to be effectively in contact with reservoir 606.

Further, in addition to slit 616 providing an exit path for vacuum line 151b, slit 616 also provides an additional function. More specifically slit 616 permits viewing of the tissue collector 58, which is preferably constructed of transparent or translucent material, while positioned within cooling system 600. With this configuration, a user will be able to determine when tissue collector 58 is full of tissue samples.

When tissue collection is complete, vacuum line 151b may be disconnected from hose fitting 59b and vacuum line 151a may be disconnected from tissue resection device 40, while leaving tissue collector 58 within cooling system 600, thereby maintaining the tissue samples in a sterile/aseptic environment, at an appropriate temperature. In operation, upon completion of tissue resection, tissue collector 58 is detached from cap member 76 and tissue filter 68, holding tissue samples therein, may be removed from tissue collector 58. In some arrangements, tissue samples will be removed from tissue filter 68, while in the operating room and placed in a suitable container for transport. In other arrangements, tissue filter 68 is removed in a suitable laboratory.

Moreover, as described above, to maintain an aseptic environment for the tissue samples, connector element 522 may be looped around and reattached to hose fitting 159, such that hose fitting 159 is received with open proximal end 524 to create a closed environment. This can be done, provided tubing 151b is sufficiently long enough, while tissue collector 58 remains disposed within cooling system 600, thereby maintaining the tissue samples at an appropriate temperature.

Another exemplary embodiment of a temperature controlled system 700 is shown in FIGS. 8-17. Similar to temperature controlled system 600, temperature controlled system 700 is utilized in those embodiments where tissue collector 58 is remotely connected to a tissue cutting device, like tissue cutting device 40, as shown in FIG. 2. However, it is understood that temperature controlled system 700 may be used with a variety of cutting systems, and its use is not limited to tissue cutting device 40. Further, temperature controlled system 700 may also be used with tissue preservation system 500, though it is not required to be so used.

Figure 15:
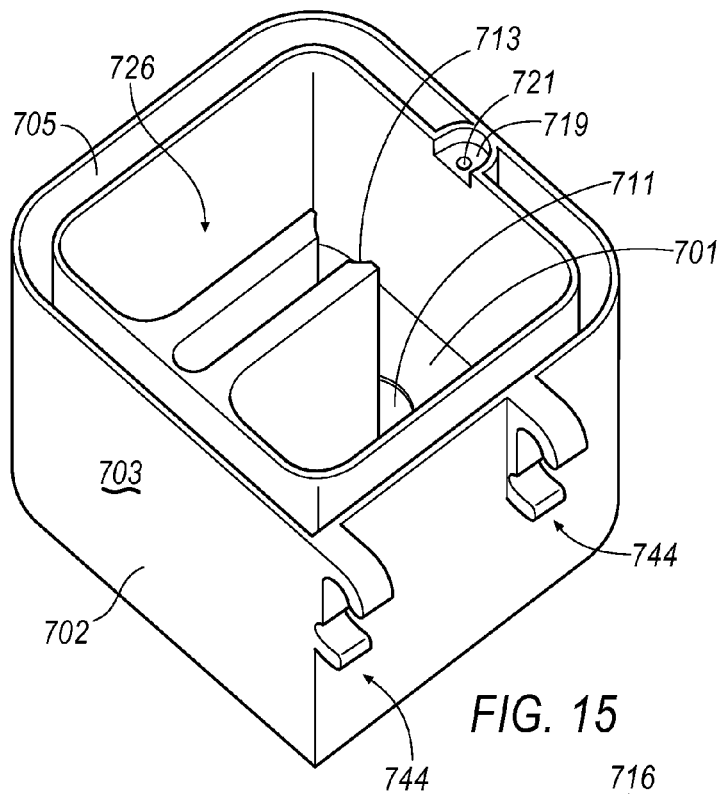
FIG. 15 is a perspective view of a base member of a tissue preservation system.
Figure 16:
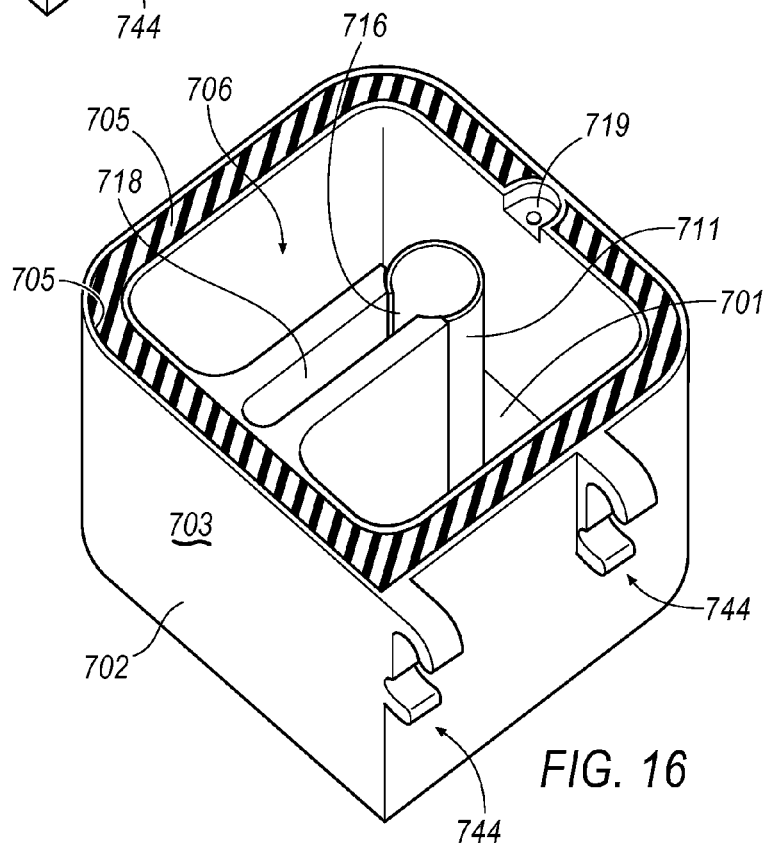
FIG. 16 is another perspective view of a base member of a tissue preservation system.

Tissue preservation system 700 includes a base member 702 and a lid 704. Base member 702 is configured as an insulated member that comprises a reservoir 706 and a tissue collector chamber 708. In one exemplary arrangement, base member 702 is generally defined by a bottom surface 701 and at least one upstanding wall member 703. In one arrangement, as explained below with respect to FIGS. 15 and 16, wall members 703 may be constructed to be generally hollow so as to form a channel 705 therein. Channel 705 may be filled with an insulating material. Wall member 703 may be a singular wall member configured to surround reservoir 706. Wall member 703 may include a plurality of wall members, each defining a separate channel 705. Additionally, as shown in FIGS. 15 and 16, a plurality of wall members collectively defining a channel 705 may surround a reservoir 706. While base member 702 is shown to be cubical, other shapes may be formed from wall members 703. For example, the base member 702 may be cylindrical, spherical, etc. Tissue collector chamber 708 is defined by a sleeve member 712. Sleeve member 712 is constructed of a thermally conductive material, as will be explained in further detail below. Sleeve member 712 is arranged such that it is in direct contact with any material that is contained within reservoir 706.

Sleeve member 712 further defines a slit 716. In one exemplary arrangement, slit 716 is configured to extend from a top edge 715 of sleeve member 712 to a bottom edge (not shown) of sleeve member 712. Slit 716 is sized to permit vacuum line 151b to extend therethrough. However, in one exemplary arrangement, sleeve member 712 is configured to be selectively removed from base member 702, and in such an arrangement, slit 716 need not extend the entire length of sleeve member 712. Instead, slit 716 may extend upwardly from the bottom edge of sleeve member 712, a sufficient distance to permit vacuum line 151b to extend outwardly from an interior of sleeve member 712.

Figure 8A:
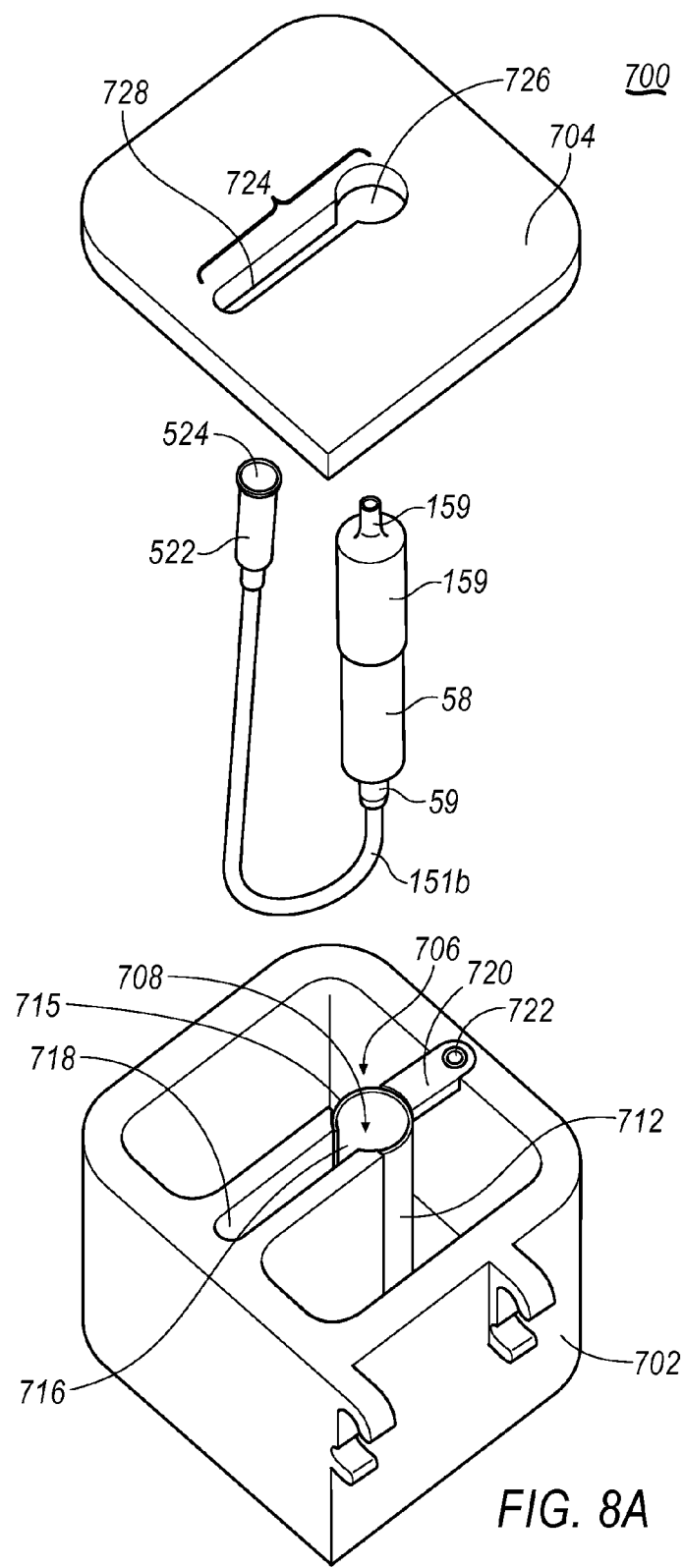
FIG. 8A is an exploded view of an exemplary temperature controlled system for use with a tissue collector.
Figure 8B:
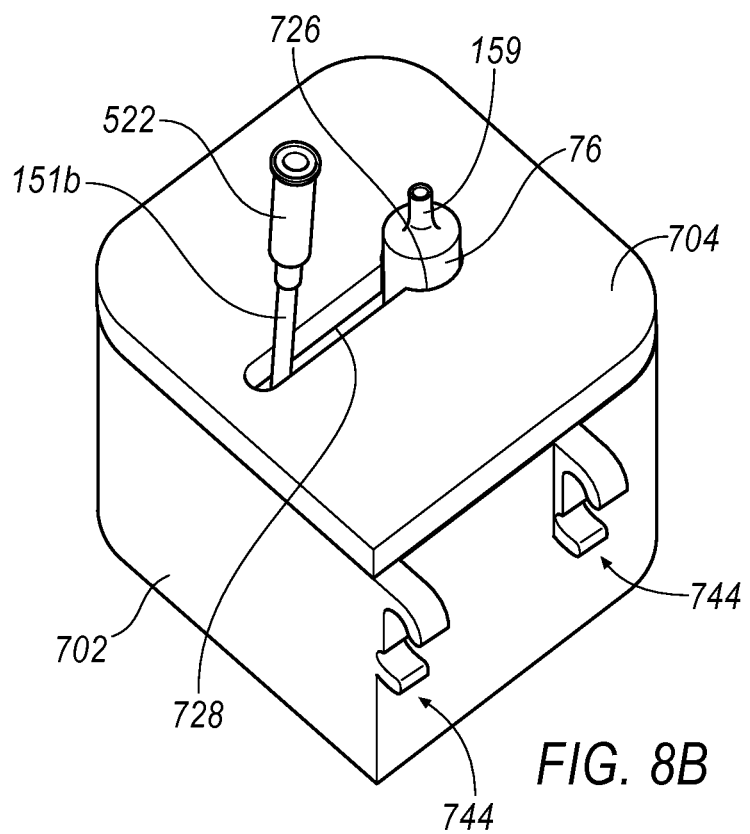
FIG. 8B is a perspective view of the temperature controlled system of FIG. 8A with the tissue collector positioned therein.

Lid 704 is sized to fit over base member 702 to retain materials positioned within reservoir 706, as well as to retain tissue collector 58 therein. To that end, lid 704 further includes an opening 724 through which both hose fitting 59 and vacuum line 151b may extend, when tissue collector 58 is positioned within tissue collection chamber 708. In one embodiment, opening 724 is comprised of at least two sections, a first section 726 and a second section 728. First section 726 is sized and shaped such that cap member 76 may at least partially extend through lid 704 when lid 704 is attached to base member 702. Second section 728 is in communication with first section 726, and is sized to permit vacuum line 151b to extend therethrough, as best seen in FIG. 8B. Further, second section 728 is sufficiently elongated to permit movement of vacuum line 151b, as will be explained in further detail below. As explained, lid 704 may be insulative to maintain the temperature of the materials within reservoir 706.

Base member 702 may be formed as a unitary member. In addition to reservoir 706, base member 702 further includes a narrow channel 718. Channel 718 is defined by two opposing walls 717a, 717b and an external wall of base member 702. Opposite the external wall of base member 702 is open to provide a passageway that is in communication with slit 716 of sleeve 712. The ends of walls 717a, 717b may be contoured to provide a seat 713 for portions of sleeve member 712, as shown in FIG. 10, for example.

Figure 9:
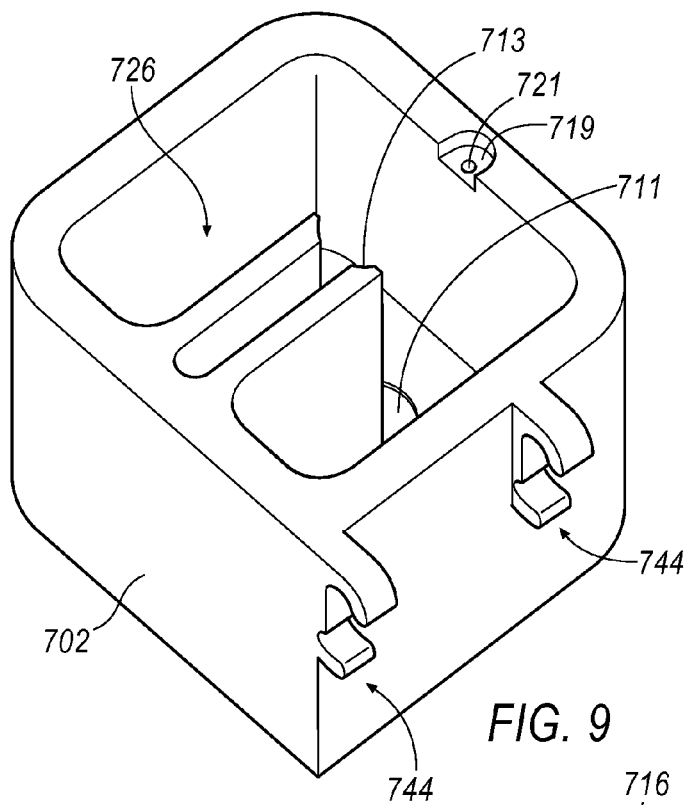
FIG. 9 is a perspective top view of a base member of the temperature controlled system of FIGS. 8A-8B.

As shown in FIG. 9, a bottom surface 729 of reservoir 706 may having a locating depression 711 formed therein. Locating depression 711 serves as a seat to ensure proper positioning of sleeve member 712 within reservoir 706.

Figure 10:
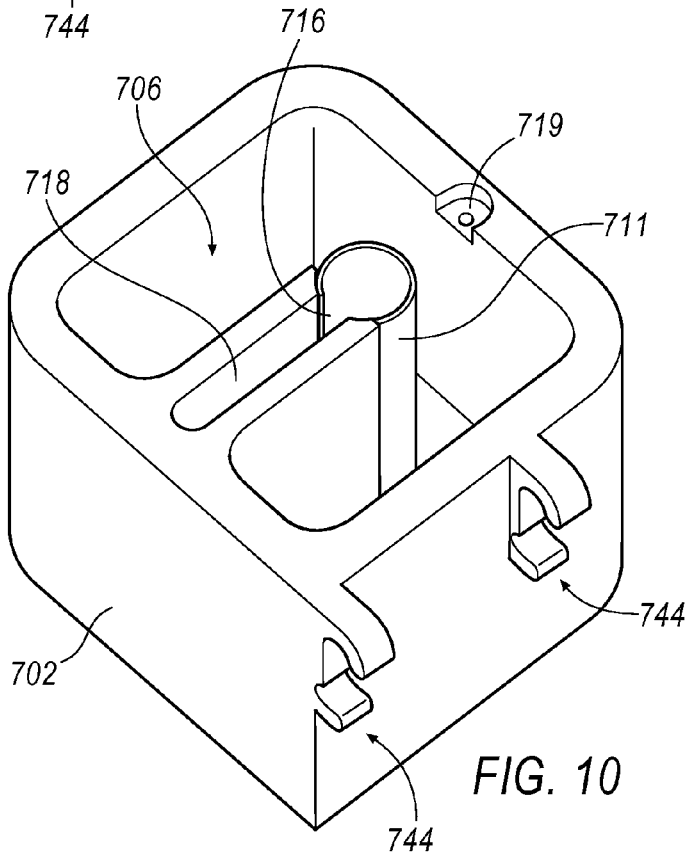
FIG. 10 is a perspective top view of the base member of FIG. 9, with a sleeve member disposed therein.

As best seen in FIGS. 9-10, a top edge 731 of base member 702 may be provided with a mounting depression 719. Mounting depression 719 further includes an engagement opening 721 for receiving a fastening element therein. Mounting depression 719 is located opposite channel 718 and is configured to receive a securing bracket 720 (best seen in FIG. 11).

Securing bracket 720 is configured to engage sleeve member 712 and secure sleeve member 712 within base member 702. To that end, one end of securing member 720 is contoured so as to correspond to the shape of sleeve member 712. The opposite end of securing member 720 is configured to be received within mounting depression 719 such that securing member 720, once installed, is generally flush with the top edge 731 of base member 702. A fastening element 722 is received within engagement opening 721 formed in mounting depression 719.

Figure 12:
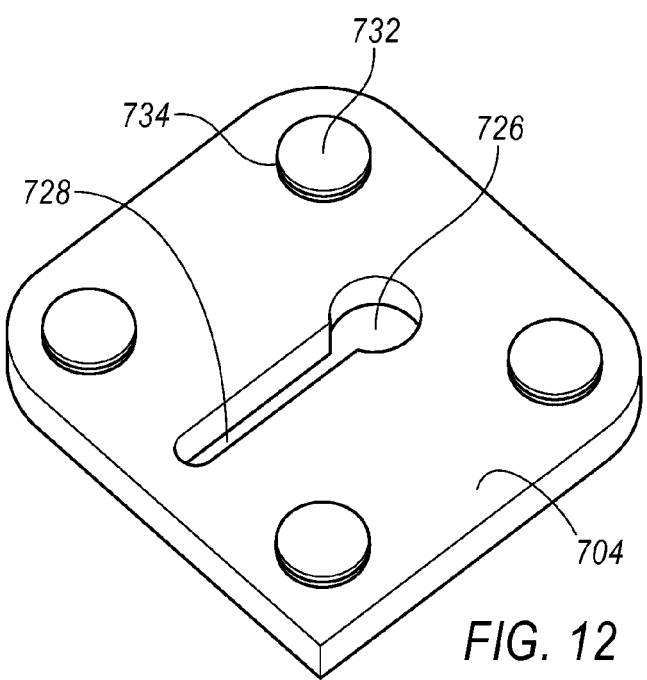
FIG. 12 is a perspective view of the bottom of a lid of the temperature controlled system of FIG. 8.
Figure 13:
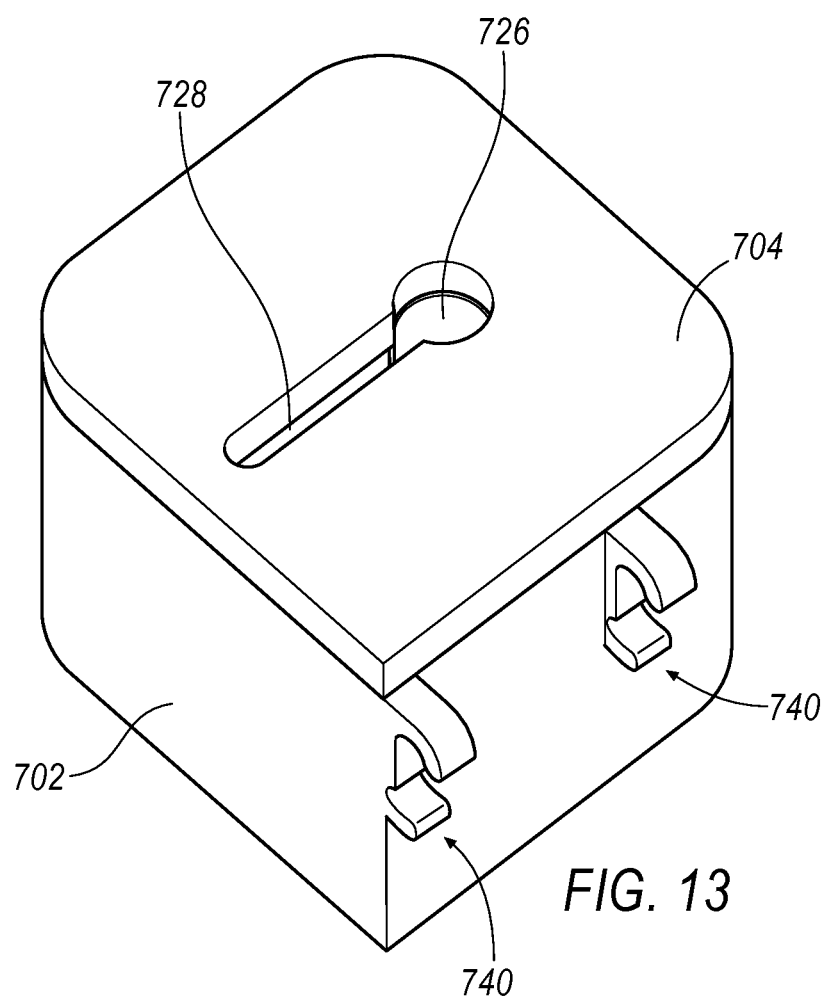
FIG. 13 is a perspective view of the temperature controlled system of FIGS. 8A-8B with the lid assembled to the base member.

Referring to FIG. 12, a bottom surface of lid 704 is provided with at least one projecting elements 732 configured to fit within an opening of reservoir 706. A seal member (not shown) may be provided around a peripheral edge 734 of projecting elements 732 to provide a water tight/sealed chamber. In one exemplary arrangement, a plurality of projecting elements 732 are provided and arranged so as to be disposed within each corner of reservoir 706. While shown as being configured as generally circular discs, the disclosure is not so limited. For example, projecting members may be configured similar to that which is shown in temperature controlled system 600. As yet another alternative arrangement, a single projecting member may be formed as a U-shaped member that extends around the periphery of lid 704. As with temperature controlled system 600, an external latching member may be provided to secure lid 704 to base member 702.

Figure 11:
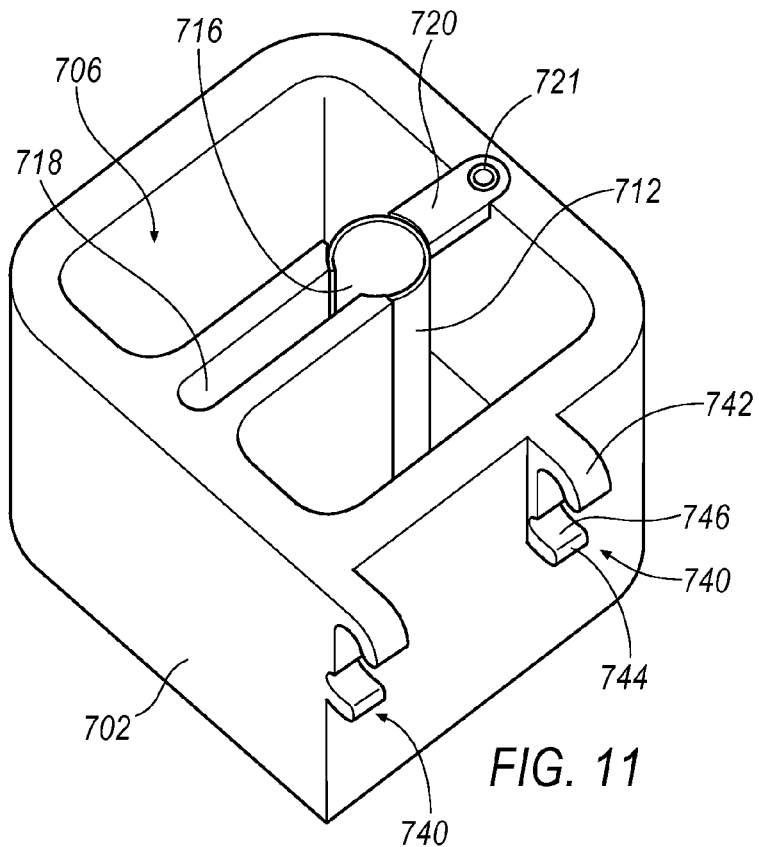
FIG. 11 is a perspective top view of the base member of FIG. 9, with the sleeve member secured therein.
Figure 14:
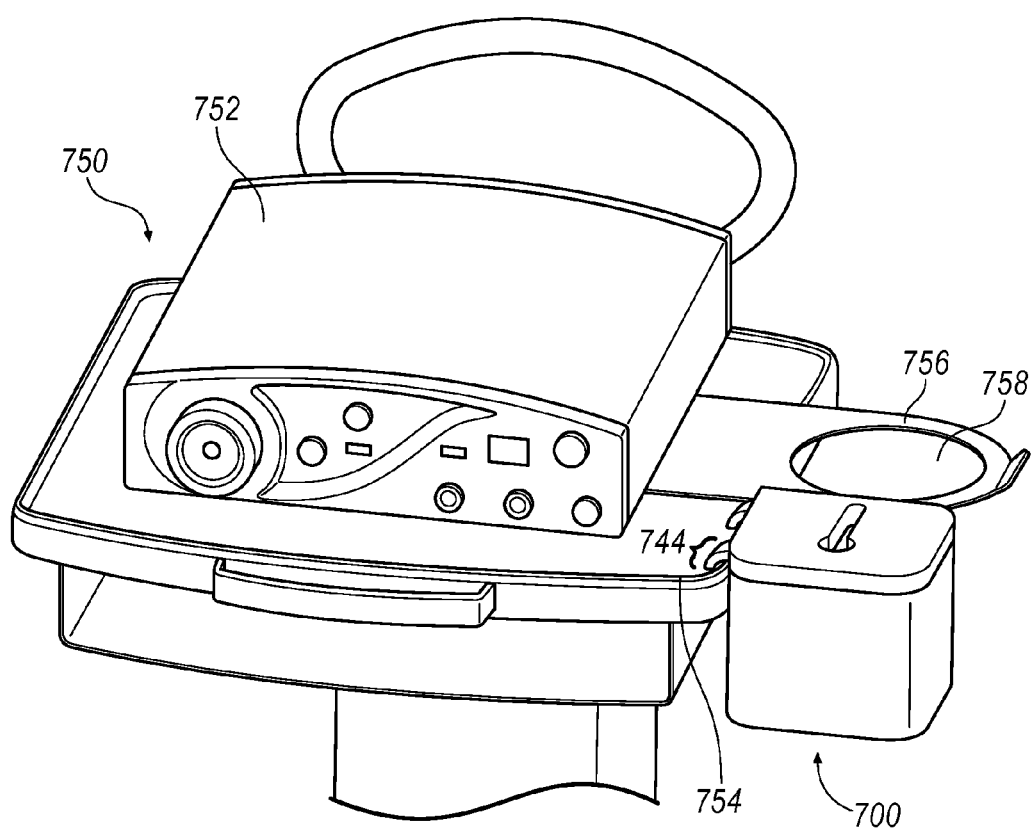
FIG. 14 is a perspective view of the temperature controlled system of FIGS. 8A-8B with the temperature controlled system secured to a surgical tray.

Referring to FIG. 11, base member 702 may further be provided with one or more clip members 744. Clip members 740 are configured to attach to a surgical try (as shown in FIG. 14, for example). In one exemplary arrangement clip members 740 are integrally formed with one external surface of base member 702. Each clip member 740 includes a top arm member 742 and a bottom arm member 744. Top arm member 742 cooperates with bottom arm member 744 to define an engagement groove 746 that is configured to receive a lip 754 of a surgical tray 750, as shown in FIG. 14. While shown in the FIGS. as having one clip member 740 positioned flush with an edge of an external surface, it is understood that the disclosure is not so limited.

As shown in FIG. 14, temperature controlled system 700 may be secured to a lip 754 of surgical tray 750. Surgical tray 750 may also retain a console 752 for operating tissue cutting device 40 (or other suitable tissue cutting device). Surgical tray 750 may also be provided with a collection canister armature 756 that includes an opening 758 to receive and support a collection canister for fluids drawn through tissue collector 58. As may be seen, in one exemplary arrangement, temperature controlled system 700 is positioned adjacent to collection canister armature 756, which will positioned collector element 522 close to the collection canister during operation, thereby minimizing the likelihood of tubing to be accidently disconnected from the collection canister, as well as removing tripping hazards within the surgical space.

In operation, base member 702 may be provided from the manufacturer with sleeve member 712 preassembled thereto, including having securing member 720 attached to secure sleeve member 712 properly within base member 702. Lid 704 is removed from base member 702 to expose reservoir 706. Reservoir 706 is filled with a suitable temperature controlling medium, such as, for example, refrigerant (i.e., ice or other suitable liquid). Lid 704 may be tethered to base 702 and thus may remain adjacent to base 702. This is described in more detail with respect to FIG. 17. Tissue collector 58 is positioned within tissue collector chamber 708 within sleeve member 712 such that cap member 76 is extending upwardly from sleeve member 712 and vacuum line 151*b* is extending out of slit 716 and into channel 718. Connector element 522 is extended through first opening 726 of lid 704 and vacuum line 151*b* is moved into second opening 728 such that connector element 522 is positioned above a top surface of lid 704. Lid 704 is then re-attached to base member 702, sealing reservoir 706. Hose fitting 159 is extending upwardly from lid 704 through first opening 726 and is connected via vacuum line 151*a* to a tissue resection device, such as tissue cutting device 40.

Due to the thermo-conductivity of sleeve 712, and because sleeve 712 is in direct communication with the temperature controlling medium positioned within reservoir 706, tissue collector 58 (and hence any tissue samples positioned therein) are kept at a suitable temperature to maintain tissue viability. Moreover, since reservoir 706 for the temperature controlling medium is insulated and water tight, refrigerants which may be used can be directly placed into reservoir 706 and replenished as necessary during use. Further, in another exemplary configuration, base member 702 may be provided with an external temperature gauge, similar to that shown with temperature controlled system 600. Alternatively, a sensor may be positioned within reservoir 702 to provide temperature readings to an external control system.

As shown in FIG. 15, base member 702 is generally defined by a bottom surface 701 and upstanding wall members 703. In one arrangement, as explained below with respect to FIGS. 15 and 16, wall members 703 may be constructed to be generally hollow so as to form a channel 705 therein. Channel 705 may form an air gap and serve as an insulator.

Additionally or alternatively, as shown in FIG. 16, the channel 705 may be filled with an insulating material 770. Material 770 may be an insulative material and include high heat resistance properties and may also be moisture resistant. Insulating material 770 may include expandable foam whereby when introduced to the channel 705, may expand to at least substantially fill the channel 705. Material 770 may also include any one or combination of fiberglass, polyurethane, polystyrene, polyisocyanurate, silicone, wool, plastic fibers, cellulose, etc. Material 770 may also include a liquid configured to further provide insulative properties to reservoir 706. For example, the liquid may include a coolant or refrigerant. Additionally or alternatively, channel 705 may be lined with a barrier liner (not shown) to further aid in insulation. For example, the barrier liner may include plastic or foil film. Channel 705 may be formed via injection molding, stamping, extruding, etc. Channel 705 may aid in keeping reservoir 706 at a suitable temperature.

As with temperature controlled system 600, when tissue collection is complete, vacuum line 151*b* may be disconnected from hose fitting 159 and vacuum line 151*a* may be disconnected from tissue resection device 40, while leaving tissue collector 58 within cooling system 700, thereby maintaining the tissue samples in a sterile/aseptic environment, at an appropriate temperature. Further, as described above, to maintain an aseptic environment for the tissue samples, connector element 522 may be looped around and reattached to hose fitting 159, such that hose fitting 159 is received with open proximal end 524 to create a closed environment, while tissue collector 58 remains disposed within cooling system 700, thereby maintaining the tissue samples at an appropriate temperature, while also maintaining a aseptic environment.

Figure 17:
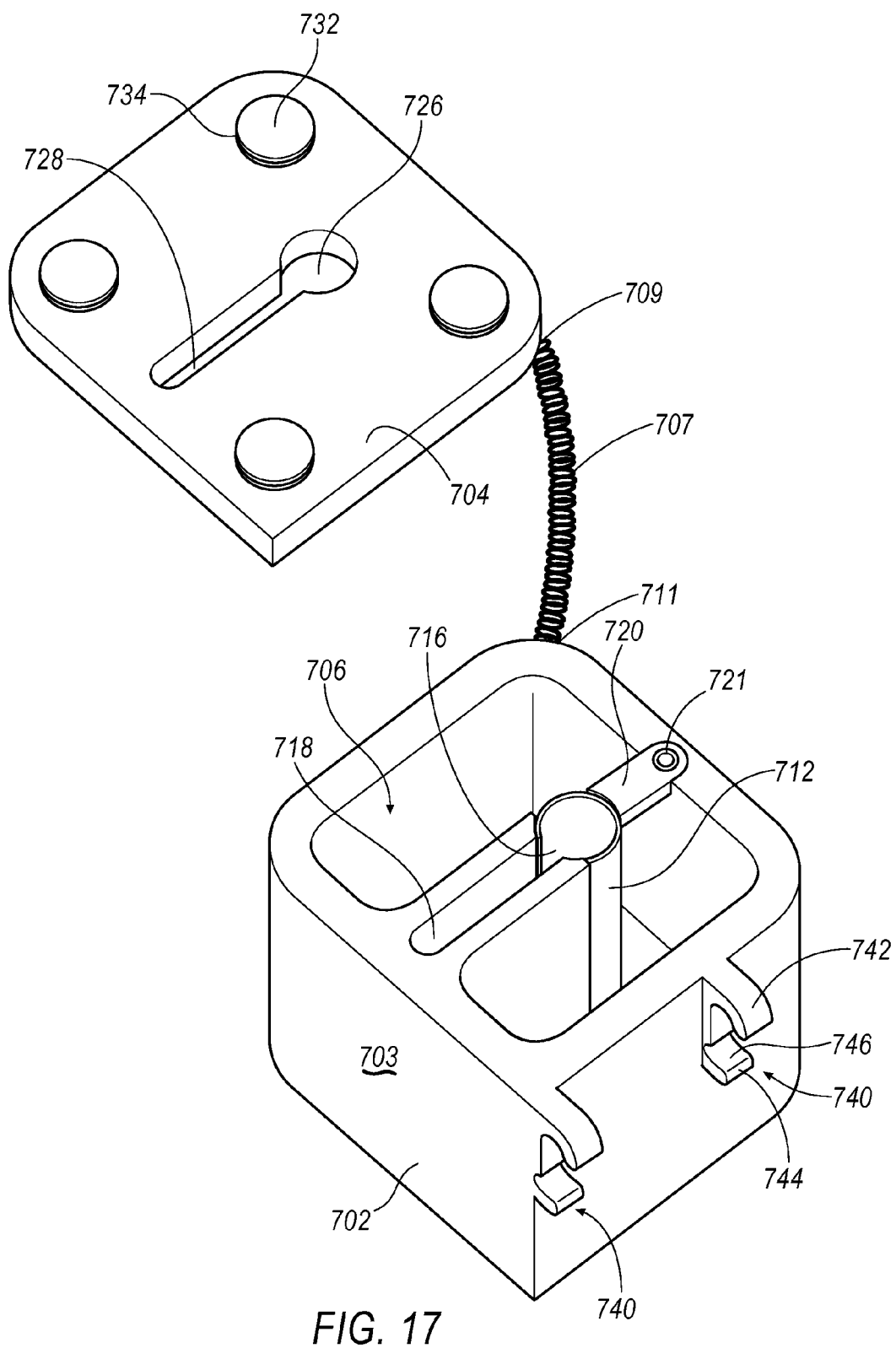
FIG. 17 is an exploded perspective view of the tissue preservation system including a lid and base member.

As shown in FIG. 17, lid 704 is tethered to base member 702. A tether 707 may have a first end 709 fixed or otherwise bonded to lid 704, and a second end 711 fixed or otherwise bonded to base 702. In this manner, lid 704 does not get misplaced or separated in the surgical suite. Tether 707 may include a cord or rope. The tether may also include a wire, plastic cable, or other flexible mechanism. Tether 707 may be at least partially retractable wherein tether 707 may include a cord and a retractable wheel. During removal of lid 704 from base 702, the cord may be pulled from the wheel. Upon placement of lid 704 on base 702, the cord may retract around the wheel. Thus, the cord may be stored securely within the wheel during procedures.

It will be appreciated that the tissue cutting devices, cooling systems and tissue preservation systems and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A tissue thermal system, comprising:
    a base member defined by a pair of inner and outer wall members that are spaced apart from one another to define a hollow channel extending around a perimeter of the base member, and wherein the inner wall member defines a reservoir configured to receive a cooling medium;
    a lid member configured to be selectively attached to the base member to close the reservoir, the lid member having an opening formed through the lid member;
    a temperature control sleeve disposed within the base member, the temperature control sleeve at least partially defining a tissue collector chamber;
    wherein the temperature control sleeve is in communication with the reservoir, while the tissue collector chamber is not in communication with the reservoir; and
    wherein the opening in the lid is in communication with the tissue collection chamber when the lid is attached to the base member.

2. The tissue thermal system of claim 1, wherein insulating material configured to further insulate the reservoir to maintain a suitable temperature is disposed within the channel.

3. The tissue thermal system of claim 2, wherein the insulating material includes expandable foam configured to substantially fill the channel.

4. The tissue thermal system of claim 1, wherein the lid member is tethered to the base member via a tether.

5. The tissue thermal system of claim 4, wherein the tether is bonded to the lid member at a first end.

6. The tissue thermal system of claim 1, wherein the tissue collector chamber is configured to receive a tissue collector configured to house tissue samples and further wherein the temperature of the tissue collector chamber is maintained at least in part by the cooling medium of the reservoir.

7. The tissue thermal system of claim 1, wherein the base member further comprises a locating depression formed on a bottom surface of the reservoir, wherein the locating depression is receives the temperature control sleeve therein.

8. The tissue thermal system of claim 1, further comprising a securing member configured to contact the temperature control sleeve and secure the temperature control sleeve to the base member.

9. The tissue thermal system of claim 1, further comprising an inner channel having an inner channel opening that is in communication with the tissue collection chamber, the inner channel extends inwardly into the reservoir, from one of the inner wall members.

10. The tissue thermal system of claim 9, wherein the opening of the lid includes a first section and a second section, wherein the second section is in communication with the inner channel and the first section is in communication with the tissue collection chamber.

11. The tissue thermal system of claim 1, wherein cooling medium disposed within the reservoir extends circumferentially around the temperature control sleeve.

12. The tissue thermal system of claim 1, wherein the opening of the lid includes a first section and a second section, wherein the first section is in communication with the tissue collection chamber.

* * * * *